US008629321B2

(12) United States Patent
Sallaud et al.

(10) Patent No.: US 8,629,321 B2
(45) Date of Patent: Jan. 14, 2014

(54) GENES ENCODING Z,Z-FARNESYL DIPHOSPHATE SYNTHASE AND A SESQUITERPENE SYNTHASE WITH MULTIPLE PRODUCTS AND USES THEREOF

(75) Inventors: Christophe Sallaud, Montpellier (FR); Denis Rontein, Greoux Les Bains (FR); Alain Tissier, Pertuis (FR)

(73) Assignee: Philip Morris Products S.A., Neuchatel (CH)

( * ) Notice: Subject to any disclaimer, the term of this patent is extended or adjusted under 35 U.S.C. 154(b) by 665 days.

(21) Appl. No.: 12/593,688

(22) PCT Filed: Apr. 2, 2008

(86) PCT No.: PCT/FR2008/050576
§ 371 (c)(1), (2), (4) Date: Sep. 29, 2009

(87) PCT Pub. No.: WO2008/142318
PCT Pub. Date: Nov. 27, 2008

(65) Prior Publication Data
US 2010/0138954 A1      Jun. 3, 2010

(30) Foreign Application Priority Data

Apr. 3, 2007  (FR) ..................................... 07 54235

(51) Int. Cl.
| C12N 15/82 | (2006.01) |
| C07K 14/415 | (2006.01) |
| C12N 15/00 | (2006.01) |
| A01H 5/00 | (2006.01) |
| A01H 5/10 | (2006.01) |

(52) U.S. Cl.
USPC ........ 800/278; 435/468; 435/320.1; 435/419; 530/350; 800/317; 800/323; 800/317.3; 800/298

(58) Field of Classification Search
None
See application file for complete search history.

(56) References Cited

U.S. PATENT DOCUMENTS

| 6,730,826 B2 | 5/2004 | Wagner et al. |
| 2004/0234968 A1 | 11/2004 | Croteau et al. |
| 2004/0249219 A1 | 12/2004 | Saucy |
| 2008/0281135 A1 | 11/2008 | Tissier et al. |
| 2009/0300791 A1 | 12/2009 | Tissier et al. |

FOREIGN PATENT DOCUMENTS

| WO | WO 93/07266 A1 | 4/1993 |
| WO | WO 99/19460 A1 | 4/1999 |
| WO | WO 99/38957 A1 | 8/1999 |
| WO | WO 00/17327 A3 | 3/2000 |
| WO | WO 01/20008 A2 | 3/2001 |
| WO | WO 2004/111183 | 12/2004 |
| WO | WO 2004111183 | * 12/2004 |
| WO | WO 2006/040479 | 4/2006 |

OTHER PUBLICATIONS

Kharel & Koyama, 2003, Nat. Prod. Rep., 20:111-118; see pp. 115-116.*
Vandermoten et al, 2009, Cell & Mol. Life Sci., 23:3685-95; see p. 3687.*
Schilmiller et al, 2009, PNAS, 106:10865-10870, see pp. 10866-10867.*
Lohr et al, 2012, Plant Science, 185-186:9-22, see p. 18.*
Ambo et el., 2008, Biochem. Biophys. Res. Commun., 375:436-440; see p. 436.*
Aharoni, A. et al. "Terpenoid Metabolism in Wild-Type and Transgenic Arabidopsis Plants" *The Plant Cell*, Dec. 2003, pp. 2866-2884, vol. 15.
Besumbes, O. et al. "Metabolic Engineering of Isoprenoid Biosynthesis in *Arabidopsis* for the Production of Taxadiene, the First Committed Precursor of Taxol" *Biotechnology and Bioengineering*, Oct. 20, 2004, pp. 168-175, vol. 88, No. 2.
Hermann, S. R. et al. "Promoters Derived from Banana Bunchy Top Virus-Associated Components S1 and S2 Drive Transgene Expression in Both Tobacco and Banana" *Plant Cell Rep*, 2001, pp. 642-646, vol. 20.
Iijima, Y. et al. "The Biochemical and Molecular Basis for the Divergent Patterns in the Biosynthesis of Terpenes and Phenylpropenes in the Peltate Glands of Three Cultivars of Basil" *Plant Physiology*, Nov. 2004, pp. 3724-3736, vol. 136.
Liu, H.-C. et al. "Cloning and Promoter Analysis of the Cotton Lipid Transfer Protein Gene *Ltp3*" *Biochimica et Biophysica Acta*, 2000, pp. 106-111, vol. 1487.
Mahmoud, S. S. et al. "Metabolic Engineering of Essential Oil Yield and Composition in Mint by Altering Expression of Deoxyxylulose Phosphate Reductoisomerase and Menthofuran Synthase" *PNAS*, Jul. 17, 2001, pp. 8915-8920, vol. 98, No. 15.
Wang, E. et al. "Elucidation of the Functions of Genes Central to Diterpene Metabolism in Tobacco Trichomes Using Post-transcriptional Gene Silencing" *Planta*, 2003, pp. 686-691, vol. 216.
Lange, B. M. et al. "Genetic engineering of essential oil production in mint" *Current Opinion in Plant Biology*, 1999, pp. 139-144, vol. 2, XP-009101099.

(Continued)

*Primary Examiner* — Anne Kubelik
*Assistant Examiner* — Jason Deveau Rosen
(74) *Attorney, Agent, or Firm* — Saliwanchik, Lloyd & Eisenschenk

(57) ABSTRACT

The present invention relates to the genes involved in the biosynthetic pathway for sesquiterpenes of SB type (alpha-santalene, epi-beta-santalene, cis-alpha-bergamotene, trans-alpha-bergamotene and endo-beta-bergamotene,) and for the precursor thereof, Z,Z-farnesyl diphosphate (Z,Z-FPP), involving a Z,Z-FPP synthase and a sesquiterpene SB synthase, and to the uses thereof for producing sesquiterpeniques compounds of SB type.

24 Claims, 8 Drawing Sheets

(56) References Cited

OTHER PUBLICATIONS

Figure 1:
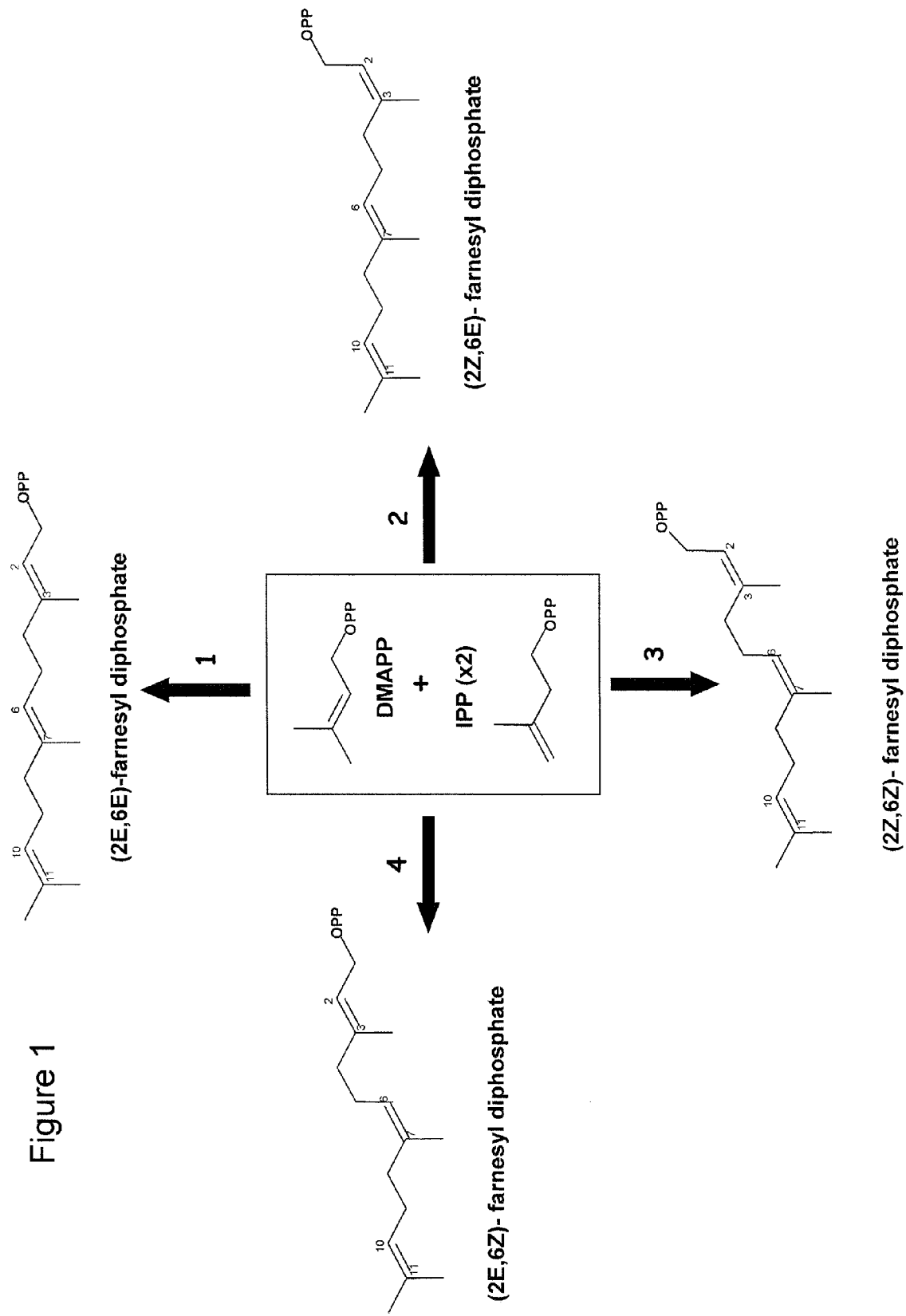

Wang, E. et al. "Isolation and characterization of the *CYP71D16* trichome-specific promoter from *Nicotiana tabacum* L." *Journal of Experimental Botany*, Sep. 2002, pp. 1891-1897, vol. 53, No. 376, XP-002318244.
Walker, K. et al. "Molecules of Interest Taxol biosynthetic genes" *Phytochemistry*, 2001, pp. 1-7, vol. 58.
Wang, E. et al. "Suppression of P450 hydrozylase gene in plant trichome glands enhances natural-product-based aphid resistance" *Nature biotechnology*, Apr. 2001, pp. 371-374, vol. 19.
Database Geneseq, Accession No. ADW26108, Ronen, G. et al. "Plant trichome expression-related DNA SEQID70", Mar. 10, 2005, XP-002459623, pp. 1-2.
Database EMBL, Accession No. AW616634, "EST323045 *L. hirsutum* trichome, Cornell University Lycopersicon hirsutum cDNA clone cLHT11N12 5', mRNA sequence", Mar. 27, 2000, XP-002459624, pp. 1-2.
Adams, S. R. et al. "Evidence for *Trans-Trans* and *Cis-Cis* Farnesyl Pyrophosphate Synthesis in *Gossipium hirsutum*" *Phytochemistry*, 1973, pp. 2167-2172, vol. 12, XP-002459621.
Heinstein, P. F. et al. "Biosynthesis of Gossypol" *The Journal of Biological Chemistry*, Sep. 25, 1970, pp. 4658-4665, vol. 245, No. 18.
Kollner, T. G. et al. "Two pockets in the active site of maize sesquiterpene synthase TPS4 carry out sequential parts of the reaction scheme resulting in multiple products" *Archives of Biochemistry and Biophysics*, 2006, pp. 83-93, vol. 448.
Database GENBANK, Accession No. AF279456, Van Der Hoeven, R. S., et al. "Genetic control and evolution of sesquiterpene biosynthesis in *Lycopersicon esculentum* and *L. hirsutum*", Dec. 21, 2000, XP-002992844, pp. 1-2.
Sallaud, C. et al. "A Novel Pathway for Sesquiterpene Biosynthesis from Z,Z-Farnesyl Pyrophosphate in the Wild Tomato *Solanum habrochaites*" *The Plant Cell*, Jan. 2009, pp. 301-317, vol. 21.

* cited by examiner

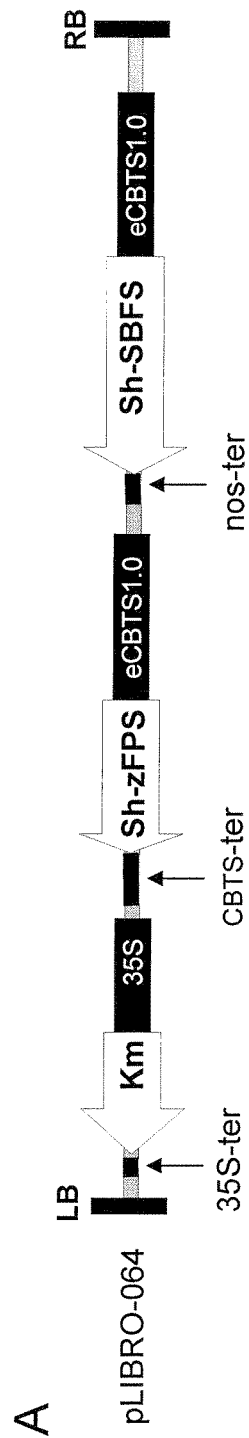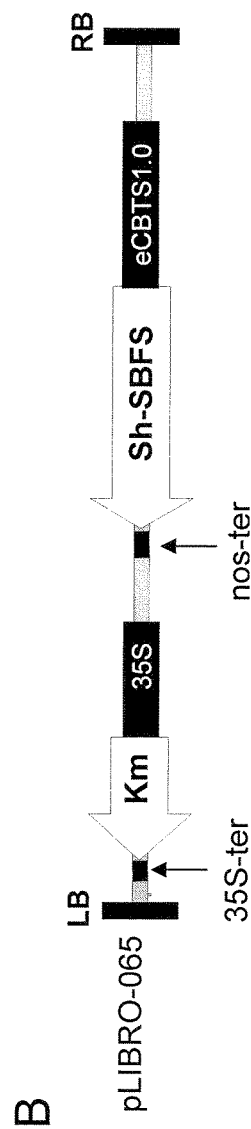
Figure 2A
Figure 2B

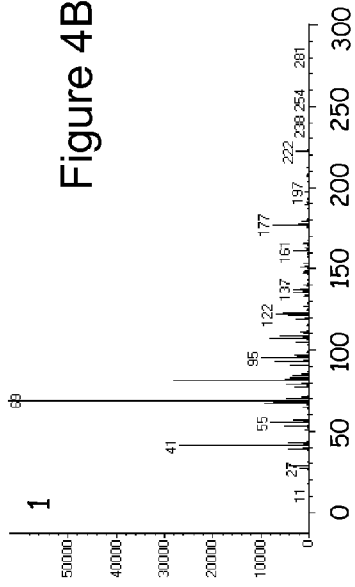
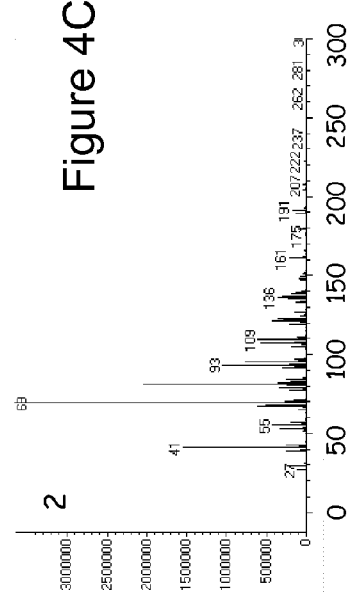
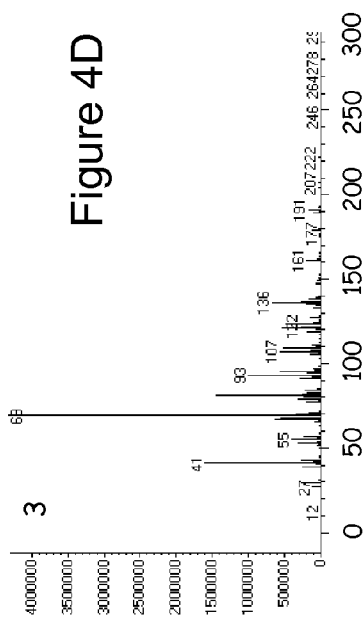
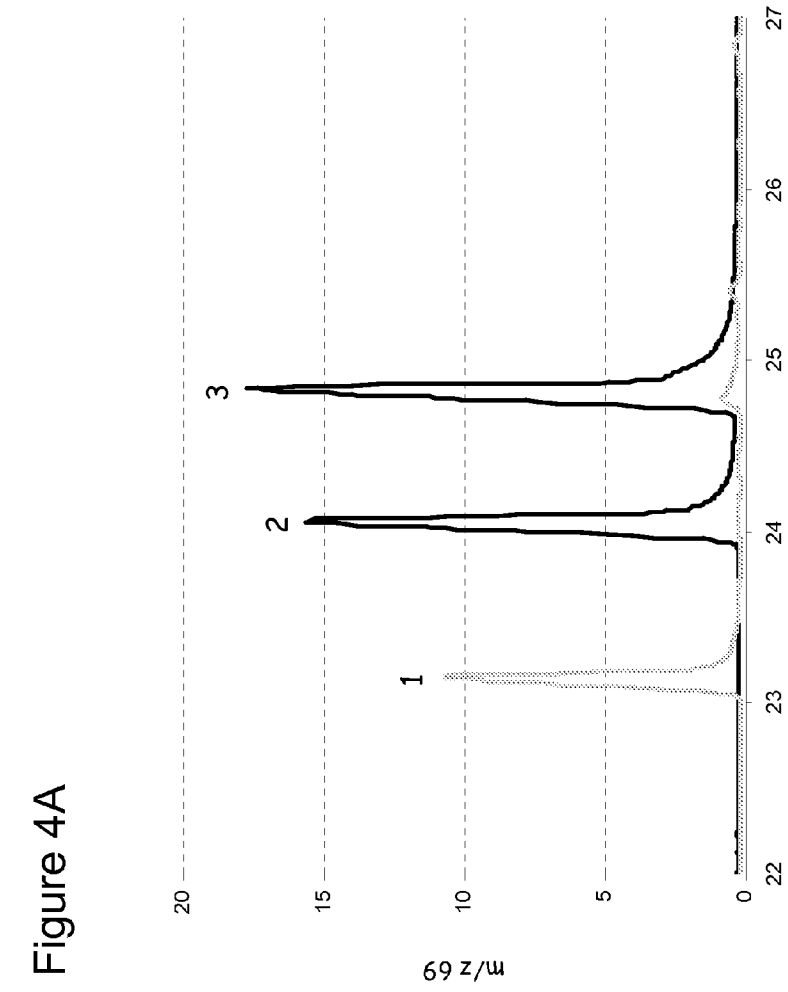
Figure 4A
Figure 4B
Figure 4C
Figure 4D

GENES ENCODING Z,Z-FARNESYL DIPHOSPHATE SYNTHASE AND A SESQUITERPENE SYNTHASE WITH MULTIPLE PRODUCTS AND USES THEREOF

CROSS-REFERENCE TO RELATED APPLICATION

This application is the U.S. national stage application of International Patent Application No. PCT/FR2008/050576, filed Apr. 2, 2008, the disclosure of which is hereby incorporated by reference in its entirety, including all figures, tables and amino acid or nucleic acid sequences.

FIELD OF THE INVENTION

The present invention relates to two genes responsible for the synthesis of a mixture of sesquiterpenes and to their use for preparing said compounds in living organisms such as bacteria, yeasts, animal cells and plants.

INTRODUCTION

Terpenes are molecules present in all living organisms such as bacteria, fungi, animals and plants. They form the largest class of natural products in the living world. In plants, these molecules play a role in primary metabolism as hormones (gibberellins, cytokinins, brassinosteroids and abscisic acid) or as compounds involved in photosynthesis (carotenoids, chlorophylls, plastoquinones and phytol), in protein prenylation processes, and in membrane structure (sterols). However, the terpenoids which arise from secondary metabolism account for most of the structural diversity of this class of molecules. The so-called secondary terpenoids play a role mainly in environmental interactions such as for example attraction of insects beneficial to the plant (pollination and predators of phytophagous insects), defense against pathogens and insects and protection against photooxidative stress (Tholl, 2006).

Terpenes are composed of multiples of 5-carbon isoprenyl units. According to the number of isoprenyl units contained, terpenes are classified as monoterpenes (compounds with ten carbon atoms or C10), sesquiterpenes (C15), diterpenes (C20), sesterterpenes (C25), triterpenes (C30), tetraterpenes (C40), and so on. The universal precursors of all terpenes are isopentenyl diphosphate (IPP) and dimethylallyl diphosphate (DMAPP). Two separate pathways lead to the formation of IPP and DMAPP. One, the mevalonate (MEV) pathway, is located in the cytoplasm of eukaryotic cells while the other, the methyl-erythritol (MEP) pathway, is known only in some bacteria and plants where it is located in chloroplasts (Rodriguez-Concepcion and Boronat, 2002). All the steps and all the genes encoding the enzymes of the steps in these two pathways are known in a certain number of organisms.

The first step of terpene biosynthesis from the common precursors IPP and DMAPP is carried out by prenyl diphosphate synthases (or prenyltransferases) which, by condensation of a homoallylic precursor, IPP, and an allylic precursor (DMAPP, geranyl diphosphate, farnesyl diphosphate or else geranylgeranyl diphosphate), generate prenyl diphosphate chains of varying length. There are two main classes of prenyl diphosphate synthases: cis-prenyltransferases or Z-prenyltransferases and trans-prenyltransferases or E-prenyltransferases. Cis-prenyltransferases lead to the formation of a double bond in cis configuration, while trans-prenyltransferases lead to the formation of a double bond in trans configuration (Koyama 1999). For instance, sequential addition of two units of IPP to DMAPP by a trans-farnesyl diphosphate synthase, or E-FPS, yields E,E-farnesyl diphosphate (E,E-FPP, C15). The chain elongation reaction begins by the formation of an allylic cation after elimination of the diphosphate ion to form an allylic prenyl. Next, one IPP is added with stereospecific elimination of a proton at position 2 to form a new C—C bond and a new double bond in the product. The repetition of this stereospecific condensation of IPP with an allylic prenyl diphosphate leads to the synthesis of a prenyl diphosphate whose chain length and stereochemistry are specific for each enzyme. In particular, the chain length of the final product can vary considerably, ranging from C10 (geranyl diphosphate) to the polyprenyl diphosphates which are precursors of natural latex composed of several thousand carbon atoms.

As mentioned earlier, prenyltransferases can be divided into two different genetic families based on the stereochemistry (E or Z) of the double bond formed after each elongation cycle (Poulter, 2006; Liang et al., 2002).

The E-prenyltransferases characterized to date lead to the synthesis of short chain prenyl phosphates (C10 to C50) having the E configuration. Examples include geranyl diphosphate synthase (GPS), farnesyl diphosphate synthase (FPS), geranyl geranyl diphosphate synthase (GGPS), octaprenyl diphosphate synthase (OPS), solanesyl diphosphate synthase (SPS) and decaprenyl diphosphate synthase (DPS) which respectively catalyze the synthesis of (E)-GPP (C10), (E,E)-FPP (C15), (E,E,E)-GGPP (C20), (E,E,E,E,E,E)-OPP (C40), (E,E,E,E,E,E,E)-SPP (C45), and (E, E,E,E,E, E,E,E,E)-DPP (C50). It should be noted that, in general, (E,E)-FPP is the substrate of the prenyltransferases responsible for the synthesis of chains with more than 20 carbons. The first characterized gene encoding an (E)-prenyltransferase was that encoding the FPS of rat (Clarke et al., 1987). Alignment of the E-prenyltransferase coding sequences has revealed two conserved motifs of DDXXD type. The three-dimensional structure of an E-prenyltransferase, determined for the first time by X-ray crystallography with FPS (Tarshis et al., 1994), as well as site-directed mutagenesis studies, have shown that the two DDXXD motifs are involved in substrate binding and the resultant catalytic activity. Lastly, it has been shown that a small number of specific amino acids, located upstream the first DDXXD motifs, determine the length of the isoprenyl chain synthesized (Wang & Ohnuma, 1999).

The first gene encoding a Z-prenyltransferase was cloned in *Micrococcus luteus* (Shimizu et al., 1998). This gene codes for an undecaprenyltransferase (UPS) which uses E-FPP as substrate to form a 55-carbon prenyl diphosphate with a Z,E stereochemistry.

This molecule is involved in the peptidoglycans biosynthesis of cell wall in some bacteria. A homologous sequence characterized in *Arabidopsis* was shown to be responsible for the synthesis of Z,E-isoprenyl diphosphate having 100 to 130 carbon atoms (Oh et al., 2000). Amino acid sequence analysis of these enzymes did not reveal any homology to the E-prenyltransferases (Koyama, 1999). In particular, Z-prenyltransferases do not possess aspartic acid-rich motifs (DDXXD). Seven conserved regions all of which more or less play a role in substrate binding and catalysis thereof have been identified. All the Z-prenyltranferases characterized to date synthesize prenyl diphosphates having a chain length higher than or equal to 55 carbons with the exception of a Z,E-FPS of *Mycobacterium tuberculosis* which uses E-GPP as substrate to form Z,E-FPP (Schulbach et al., 2000). A recent site-directed mutagenesis study on UPS of *M. luteus* identified several amino acids that play a key role in the number of elongation cycles of the isoprenyl chain synthesized (Kharel et al., 2006).

The isoprenyl diphosphates are substrates of a class of enzymes, the terpene synthases, which catalyze the formation of the basic cyclic or acylic terpene backbones in C10 (monoterpene), C15 (sesquiterpene), C20 (diterpene), and C30 (triterpene) (Cane 1999; McMillan and Beale, 1999; Wise and Croteau, 1999). The rectional diversity of these enzymes underlies the diversity of the cyclic terpene backbones found in nature. Four stereoisomers of farnesyl diphosphate are theoretically possible according to the stereochemical configuration of the double bonds at positions 2 and 6 of the molecule (E,E, Z,E, E,Z or Z,Z). However, to date, all the sesquiterpene synthases whose genes have been characterized use E,E-FPP as substrate. This is the case for example of the 5-epi-aristolochene synthase of tobacco (Facchini & Chappell, 1992), (E)-alpha-bisabolene synthase of Abies grandis (Bohlmann et al., 1998), germacrene A synthase of chicory (Bouwmeester et al., 2002), amorpha-4,11-diene synthase of Annual Wormwood (Wallaart et al., 2001), germacrene C synthase of tomato (Colby et al., 1998), caryophyllene synthase of Annual Wormwood (Cai et al., 2002), and valencene synthase of orange (Sharon-Asa et al., 2003). Nonetheless, a recent study reported that a maize sesquiterpene synthase (tps4) which catalyzes the synthesis of a mixture of 14 sesquiterpenes accepted E,E-FPP and Z,E-FPP (Kollner et al., 2006), thereby showing that sesquiterpene synthases could use isomers other than E,E-FPP as substrates. However, none of the sesquiterpene synthases cloned so far uses Z,Z-FPP.

The type VI glandular trichomes of *Solanum habrochaites* (formerly known as *Lycopersicum hirsutum*) secrete large amounts of sesquiterpene olefins belonging to two different classes. Class I contains germacrene B in particular and class II contains among others alpha-santalene and alpha-bergamotene. Segregation analysis between a cultivated tomato genotype (*Lycopersicon esculentum=Solanum lycopersicum*) and a wild-type tomato genotype (*Lycopersicon hirsutum=Solanum habrochaites*) showed that the biosynthesis of these two different sesquiterpene classes is controlled by two different loci (Sst1A and Sst2) mapping to two different chromosomes (van der Hoeven et al., 2000). The Sst1A locus is located on chromosome 6, and the genes at this locus are responsible for accumulation of class I sesquiterpenes. The Sst2 allele of *S. habrochaites* located on chromosome 8 controls the accumulation of class II sesquiterpenes such as alpha-santalene but also cis-alpha-bergamotene, trans-alpha-bergamotene, epi-beta-santalene and beta-bergamotene and other unidentified minor compounds. Whereas the coding sequences of the genes at the Sst1A locus have been identified (van der Hoeven et al. 2000), this is not the case for those at the Sst2 locus.

SUMMARY OF THE INVENTION

The present invention relates to two genes responsible for the synthesis of a mixture of sesquiterpenes composed mainly of alpha-santalene, epi-beta-santalene, cis-alpha-bergamotene, trans-alpha-bergamotene, and endo-beta-bergamotene and their precursor Z,Z-farnesyl diphosphate (Z,Z-FPP), and to the use thereof for preparing said compounds in living organisms such as bacteria, yeasts, animal cells and plants.

More specifically, the present invention describes the identification and characterization of two genes of *S. habrochaites* responsible for the synthesis of class II *S. habrochaites* sesquiterpenes (alpha-santalene, epi-beta-santalene, cis-alpha-bergamotene, trans-alpha-bergamotene and endo-beta-bergamotene among others) which shall be referred to as SB type sesquiterpenes (for Santalene and Bergamotene) in the remainder of the text. The first gene codes for a Z,Z-farnesyl diphosphate synthase and the second for a multiple product sesquiterpene synthase which uses Z,Z-farnesyl diphosphate as substrate. Production of the corresponding recombinant proteins revealed that the sesquiterpene profile obtained in vitro is identical to that controlled by the tomato Sst2 locus.

The invention relates to the enzymatic activities involved in the biosynthesis of Z,Z-FPP from IPP and DMAPP on one hand, and of a mixture of sesquiterpenes composed mainly of alpha-santalene, epi-beta-santalene, cis-alpha-bergamotene, trans-alpha-bergamotene and endo-beta-bergamotene from Z,Z-FPP, as well as to the peptide sequences responsible for said activities and to the nucleic acid sequences encoding said peptide sequences. The invention further relates to methods using said enzyme activities for producing said compounds or derivatives thereof.

The present invention therefore relates to a method for producing a mixture of sesquiterpenes, mainly composed of alpha-santalene, epi-beta-santalene, cis-alpha-bergamotene, trans-alpha-bergamotene and endo-beta-bergamotene, from Z,Z-FPP in a cell having an IPP and DMAPP source, comprising:
  a) introducing into said cell a construct having an expression cassette comprising a first gene encoding a Z,Z-FPS according to the present invention and a construct having an expression cassette comprising a second gene encoding a sesquiterpene synthase named SBS according to the present invention;
  b) culturing the transformed cell in suitable conditions for the expression of said first and said second genes; and,
  c) optionally, collecting the Z,Z-FPP or the sesquiterpenic products of the SBS enzyme or derivatives thereof contained in said cell and/or in the culture medium.

The present invention relates to an isolated or recombinant protein having Z,Z-FPS activity. Said protein preferably has a sequence with at least 80% identity to SEQ ID No. 2.

The invention also relates to a nucleic acid comprising a nucleotide sequence encoding such protein, or a sequence capable of hybridizing thereto in stringent conditions.

The present invention also relates to an isolated or recombinant protein having a SB synthase type activity and having a sequence with at least 80% identity to SEQ ID No. 4. The invention also relates to a nucleic acid comprising a nucleotide sequence encoding such protein, or a sequence capable of hybridizing thereto in stringent conditions.

The present invention relates to an expression cassette comprising a nucleic acid according to the invention, a vector comprising an expression cassette or a nucleic acid according to the invention, a host cell comprising a vector, an expression cassette or a nucleic acid according to the invention, and a non-human transgenic organism comprising a cell, a vector, an expression cassette or a nucleic acid according to the invention.

The present invention also relates to a method for producing Z,Z-farnesyl diphosphate (Z,Z-FPP), or derivatives thereof, from IPP and DMAPP in a cell having an IPP and DMAPP source, comprising:
  a) introducing into said cell a construct having an expression cassette with a nucleic sequence encoding a Z,Z-FPS according to the present invention;
  b) culturing the transformed cell in suitable conditions for the expression of the gene; and
  c) optionally, collecting the derivative(s) thereof contained in said cell and/or in the culture medium.

The present invention relates to the use of a protein, a nucleic acid, a host cell or a transgenic organism according to the invention for preparing Z,Z-FPP or SB type sesquiterpenes, such as alpha-santalene, epi-beta-santalene, cis-alpha-bergamotene, trans-alpha-bergamotene and endo-beta-bergamotene, or derivatives thereof such as alpha-santalol, epi-beta-santalol, cis-alpha-bergamotol, trans-alpha-bergamotol and beta-bergamotol.

The present invention relates to a cell or a non-human transgenic organism, characterized in that the synthetic pathway of class II sesquiterpenes is blocked by inactivation of either the gene encoding a Z,Z-FPS according to the invention, or the gene encoding a SB synthase according to the invention, or else both genes.

The present invention also relates to the use of a nucleic acid for identifying molecular markers allowing the corresponding genomic sequences to be introduced into other species or varieties of cultivated tomato (*Solanum lycopersicum*). In the context of the present invention, the nucleotide sequences SEQ ID No. 1 and No. 2 or variants thereof can also be used as molecular markers for introgression of said sequences into other species or varieties of cultivated tomato.

Thus, the present invention relates to molecular markers comprising all or part of a nucleic acid with at least 80% identity to SEQ ID No. 1 or SEQ ID No. 3 for identifying a genomic polymorphism between *S. habrochaites* and species of the *Solanum* type sexually compatible with *S. habrochaites* so as to introduce the corresponding genes into said species. The invention also relates to a method consisting in introducing the zFPS and SBS genes into a species which is not sexually compatible with *Solanum habrochaites* by protoplast fusion.

The present invention also relates to a method for producing Z,Z-farnesol by dephosphorylation of Z,Z-FPP by a phosphatase.

LEGENDS OF FIGURES

FIG. 1: Possible stereosiomers of FPP. All stereoisomers of FPP are biosynthesized from IPP and DMAPP. To date only E,E-farnesyl diphosphate synthase (1) characterized in many organisms, and Z,E-farnesyl diphosphate synthase (2) of *Mycobacterium tuberculosis* (Schulbach et al., 2000), were known. (3): Tomato Z,Z-farnesyl diphosphate synthase according to the present invention; (4): E,Z-farnesyl diphosphate synthase: no enzyme having this activity has yet been described.

FIG. 2: Drawing of T-DNA carrying the Sh-zFPS and Sh-SBS transgenes. Km: kanamycin resistance gene; 35S: CaMV 35S gene promoter. CBTS-ter: CBTS terminator gene; eCBTS1.0: 1 kb promoter of the CBTS gene fused with the enhancer of the CaMV 35S promoter. Sh-zFPS: coding frame of the gene encoding tomato zFPS (*S. habrochaites* LA1777); Sh-SBS: coding frame of the gene encoding tomato SB synthase (*S. habrochaites* LA1777); LB: T-DNA left border; RB: T-DNA right border; 35S-ter: CaMV 35S gene terminator; nos-ter: nopaline synthase gene of *Agrobacterium tumefasciens* terminator. FIG. 2: T-DNA fragment of the pLIBRO64 binary vector; FIG. 2B: T-DNA fragment of the pLIBRO65 binary vector.

Figure 3A:
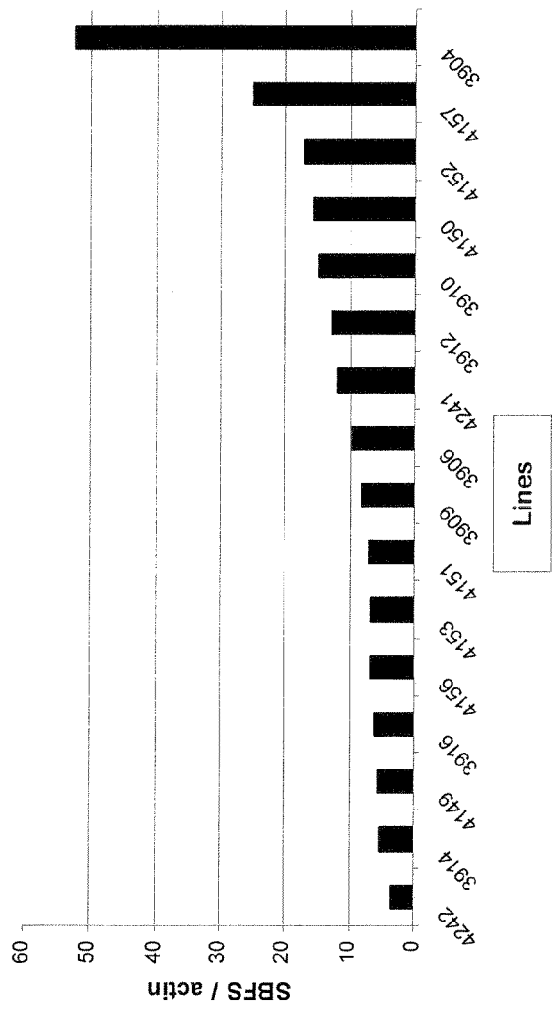
Figure 3B:
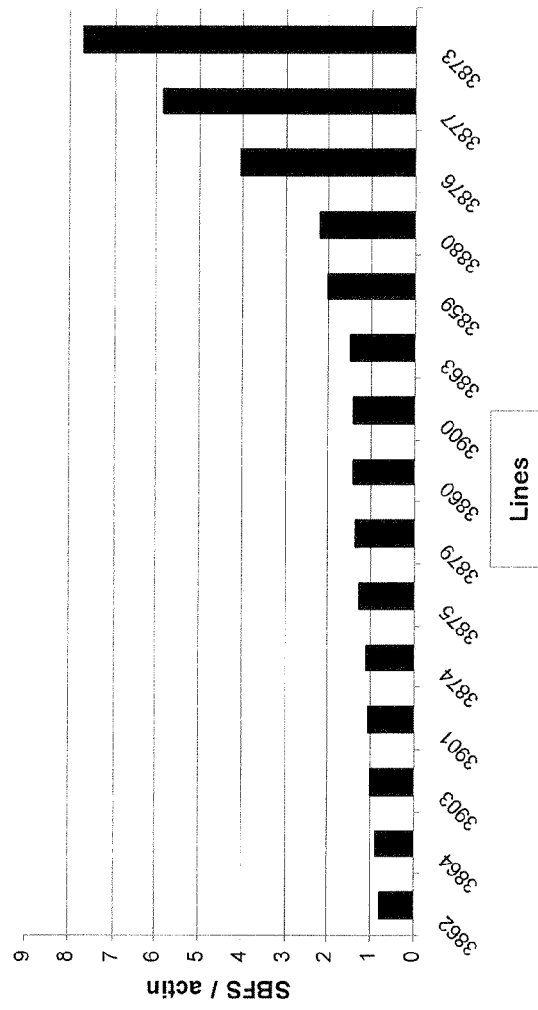

FIG. 3: Sh-SBS transgene expression analysis in transgenic tobacco leaves. Expression is determined by real time quantitative PCR using fluorescent probes (®TAQ-MAN, ABI). One probe is specific for the Sh-SBS transgene while the other is specific for the tobacco actin gene (control gene). The ordinate axis values represents the potency 2 ratios of the values obtained with the Sh-SBS probe to those obtained with the actin probe ($2^{SBS}/2^{actin}$). This ratio expresses the ratio of Sh-SBS transgene expression to that of actin. The abscissa axis values indicate the number of the transgenic lines. FIG. 3A: Transgenic tobacco lines having integrated the Sh-zFPS and Sh-SBS transgenes (pLIBRO-064). FIG. 3B: Transgenic tobacco lines having integrated only the Sh-SBS transgene (pLIBRO-065).

FIG. 4: GC/MS profile of (Z,Z)-farnesol merged on the farnesol standards (mixture of isomers). FIG. 4A: The gray chromatogram (m/z: 69) corresponds to the product obtained in vitro with the Sh-zFPS-6His recombinant protein. Sh-FPS-6His was incubated with DMAPP and IPP. The isoprenyl diphosphate product was dephosphorylated in alcohol and purified by liquid chromatography. Peak 1 corresponds to Z,Z-farnesol. The black chromatogram (m/z: 69) corresponds to the farnesol standard composed of a mixture of (Z,E)-, (E,Z)-, and (E,E)-farnesol isomers (Fluka). Peak 2 corresponds to a mixture of (Z,E)- and (E,Z)-farnesol and peak 3 to (E,E)-farnesol. FIG. 4B: Mass spectrum of (Z,Z)-farnesol corresponding to peak 1. FIG. 4C: Mass spectrum of (Z,E)- and (E,Z)-farnesol (mixture) corresponding to peak 2. FIG. 4D: Mass spectrum of (E,E)-farnesol corresponding to peak 3.

Figure 5A:
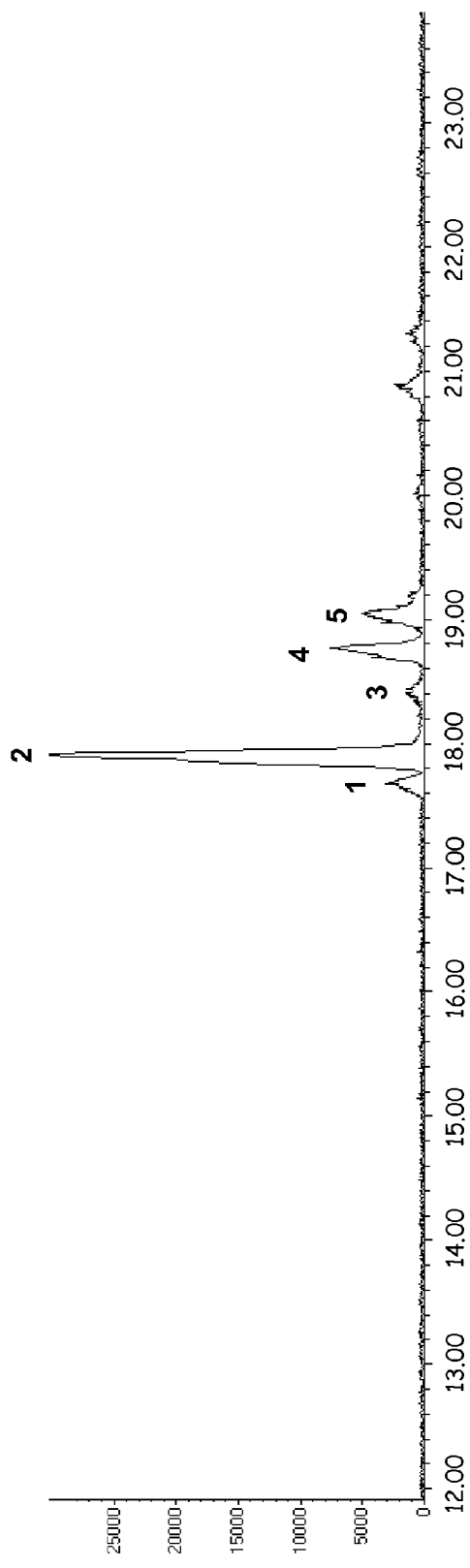
Figure 5B:
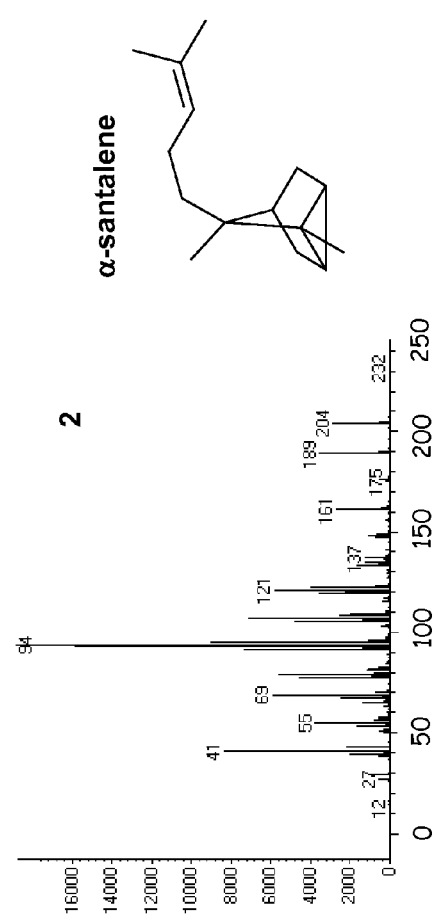

FIG. 5: GC/MS profile of in vitro activity tests carried out with Sh-zFPS-6His and Sh-SBS-6His recombinant proteins. The two recombinant enzymes Sh-zFPS-6His and Sh-SBS-6His were incubated together with IPP and DMAPP. The reaction mixture was extracted with pentane and analyzed by GC/MS. FIG. 5A: Chromatogram of the product obtained in vitro with Sh-zFPS and Sh-SBS. Peak 2 is the major product and corresponds to alpha-santalene. 1, cis-alpha-bergamotene; 2, alpha-santalene; 3, trans-alpha-bergamotene; 4, epi-beta-santalene; 5, endo-beta-bergamotene. FIG. 5B: Mass spectrum corresponding to peak 2 (left) and alpha-santalene structure (right).

Figure 6:
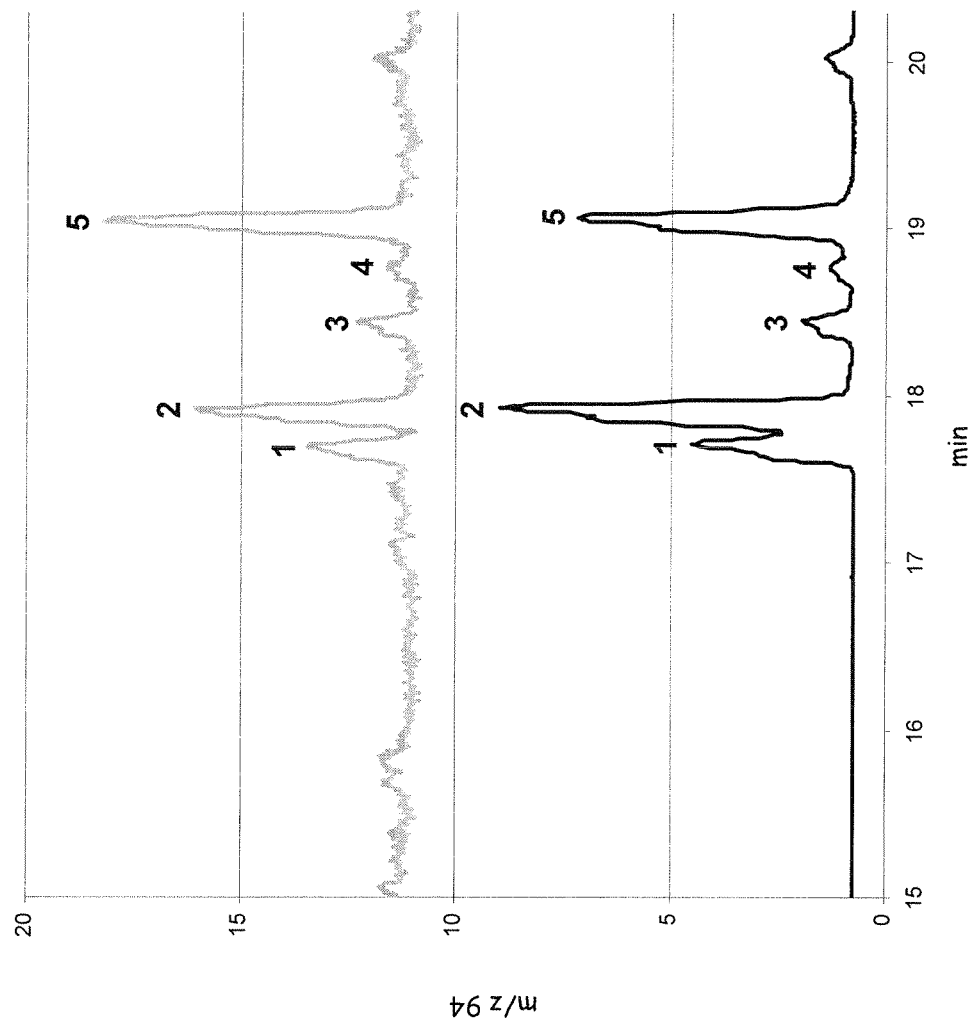

FIG. 6: Merged GC profiles with products obtained in vitro with recombinant enzymes Sh-zFPS-6His and Sh-SBS-6His, and exudate of TA517 isogenic recombinant tomato line. The tracings correspond to the extracted m/z 94 ion. Gray: olefins produced in vitro by Sh-zFPS and Sh-KS. Black: exudate of TA517 isogenic line. 1, cis-alpha-bergamotene 2, alpha-santalene; 3, trans-alpha-bergamotene; 4, epi-beta-santalene; 5, endo-beta-bergamotene.

Figure 7A:
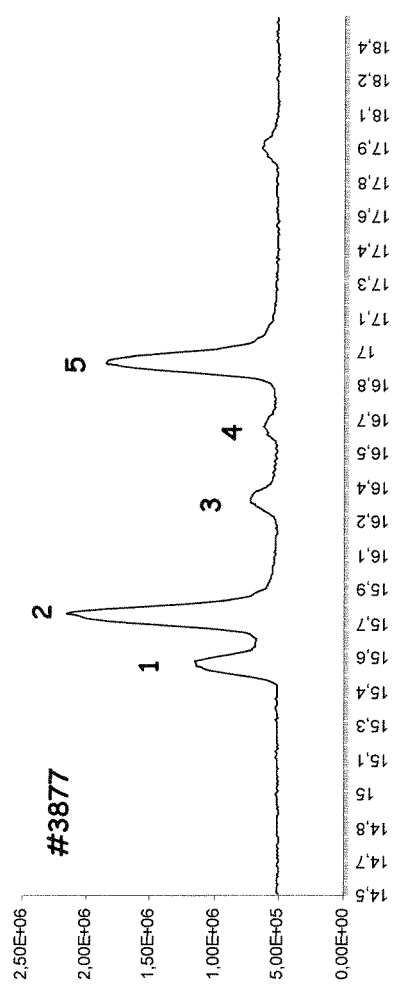
Figure 7B:
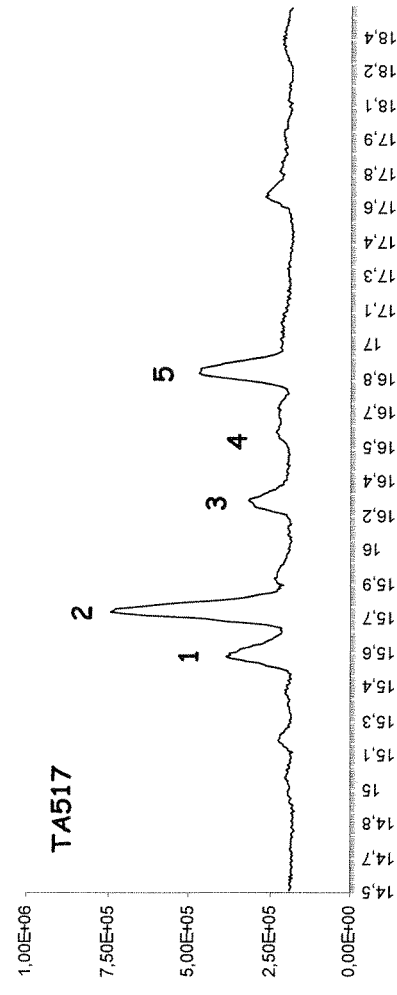

FIG. 7: GC/MS profile of volatile molecules emitted by a transgenic plant (#3877) harboring the Sh-zFPS and Sh-SBS transgenes. Transgenic plant #3877 was cultivated for 24 h in a controlled atmosphere in a culture chamber. Volatile molecules emitted by the plants were trapped on a Super® Q matrix (Alltech) and analyzed by GC/MS. The chromatogram (7A) shows several peaks with signatures characteristic of SB type sesquiterpenes. Peaks were identified by comparing their retention times and mass spectra with those of the TA517 line (7B). 1, cis-alpha-bergamotene 2, alpha-santalene; 3, trans-alpha-bergamotene; 4, epi-beta-santalene; 5, endo-beta-bergamotene.

Figure 8:
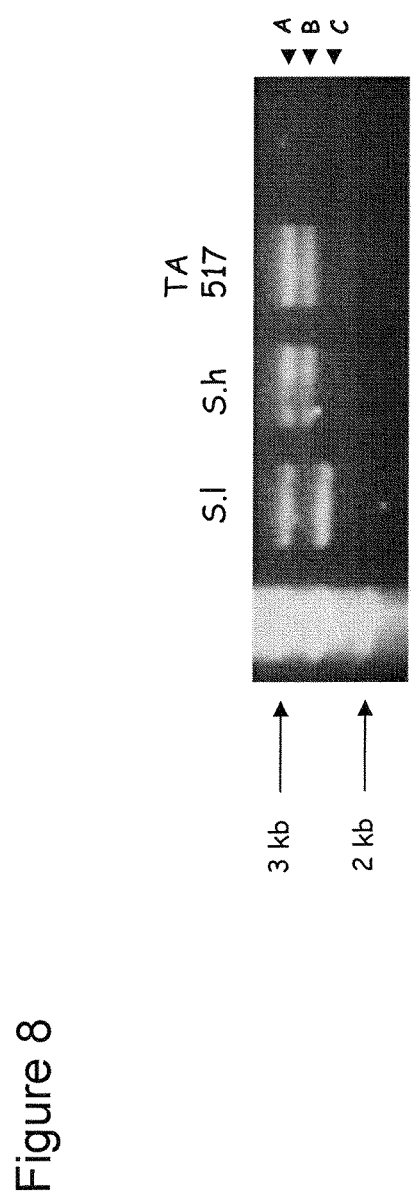

FIG. 8: zFPS gene polymorphism between *S. lycopersicum* (Sl) and *S. habrochaites* (Sh): The complete zFPS gene was amplified by PCR from genomic DNA of *S. lycopersicum, S. habrochaites* and TA517. Separation of the PCR products on a 0.8% agarose gel identified 3 bands, A, B, C, with a respective size of approximately 3,000, 2,500 and 2,000 nucleotides. The PCR product corresponding to band B is specific of the S.h genome and corresponds to the zFPS gene described herein. kb: kilobases.

ABBREVIATIONS AND DEFINITIONS mRNA: messenger ribonucleic acid
DNA: deoxyribonucleic acid cDNA: complementary DNA produced by reverse transcription of mRNA.
CaMV: cauliflower mosaic virus
DMAPP: dimethylallyl diphosphate
CBT-ol: cembratrien-ol
CBTS: cembratrien-ol synthase
GPP: geranyl diphosphate
FPP: farnesyl diphosphate
GC: gas chromatography
GGPP: geranyl geranyl diphosphate
ihpRNAi: interfering intron hairpin RNA
IPP: isopentenyl diphosphate
MS: mass spectrometry
PCR: polymerase chain reaction
RACE: rapid amplification of cDNA ends
A, R, N, D, C, Q, E, G, H, I, L, K, M, F, P, S, T, W, Y, V: standard code of amino acids according to the universal nomenclature www3.ncbi.nlm.nih.gov/Taxonomy/Utils/wprintgc.cgi?mode=t
A, C, G, T, B, D, H, K, M, N, R, S, V, W, Y: standard code of bases according to the universal nomenclature www3.ncbi.nlm.nih.gov/Taxonomy/Utils/wprintgc.cgi?mode=t
RFLP: restriction fragment length polymorphism "Z,Z-farnesyl diphosphate synthase" or zFPS, as used herein, refers to an enzyme capable of producing Z,Z-farnesyl diphosphate [(2Z, 6Z)-farnesyldiphosphate or cis,cis-FPP], from isopentenyl diphosphate (IPP) and dimethyl allyl diphosphate (DMAPP). "Z,Z-FPS activity", as used herein, refers to the production of Z,Z-farnesyl diphosphate from IPP and DMAPP. ZZ-FPS activity can be evaluated by measuring the formation of Z,Z-farnesyl diphosphate.

"SB synthase" or SBS, as used herein, refers to an enzyme capable of producing a mixture of sesquiterpenes composed mainly of alpha-santalene, epi-beta-santalene, cis-alpha-bergamotene, trans-alpha-bergamotene and endo-beta-bergamotene from Z,Z-FPP. "SB type activity" refers to the production of SB type sesquiterpenes from 4Z-farnesyl diphosphate. SB type activity can be evaluated by measuring the formation of one or more SB type sesquiterpenes. An example of determining SB type activity is described in the examples.

"SB type sesquiterpene", as used herein, refers to a mixture of sesquiterpenes composed mainly of alpha-santalene, epi-beta-santalene, cis-alpha-bergamotene, trans-alpha-bergamotene and endo-beta-bergamotene.

"Stringent hybridization conditions": Generally, for a polynucleotide of a given size and sequence, stringent conditions are obtained by working at a temperature approximately 5° C. to 10° C. below the melting temperature (Tm) of the formed hybrid, in the same reaction mixture, by said polynucleotide and its complement. Stringent hybridization conditions for a given polynucleotide can be determined by one skilled in the art according to the size and the base composition of the polynucleotide in question, and the composition of the hybridization mixture (in particular, pH and ionic strength). High stringency conditions include a wash step with 0.2×SSC buffer at 65° C.

The stringent hybridization conditions described above can be adapted by one skilled in the art for polynucleotides which are higher or smaller in size, in accordance with the relevant teachings known to one skilled in the art, described in particular in Sambrook et al., 1989, Molecular Cloning, A Laboratory Manual, Cold Spring Harbor; Maniatis et al., 1982, Molecular Cloning, A Laboratory Manual, Cold Spring Harbor Lab. CSH, N.Y. USA, or one of the recent reeditions thereof, and in Ausubel et al., Eds., 1995, Current Protocols in Molecular Biology, Chapter 2 (Greene Publishing and Wiley-Interscience, N.Y.).

"Heterologous", as used herein, is understood to mean that the gene has been introduced into the cell by genetic engineering. It can be present in episomal or chromosomal form. The gene can originate from a source different from the cell in which it is introduced. However, the gene can also come from the same species as the cell in which it is introduced but it is considered heterologous due to its environment which is not natural. For example, the gene is referred to as heterologous because it is under the control of a promoter which is not its natural promoter, it is introduced at a location which differs from its natural location. The host cell may contain an endogenous copy of the gene prior to introduction of the heterologous gene or it may not contain an endogenous copy.

As used herein, "percent identity" between two nucleic acid or amino acid sequences refers to a percentage of nucleotides or amino acid residues which are identical between the two sequences to be compared, obtained after the best alignment, said percentage being purely statistical and the differences between the two sequences being distributed randomly and throughout their length. The best alignment or optimum alignment is the alignment for which the percent identity between the two sequences to be compared, as calculated hereafter, is the highest. Sequence comparisons between two nucleic acid or amino acid sequences are conventionally carried out by comparing said sequences after optimally aligning them, said comparison being done by segment or by window of comparison in order to identify and compare local regions of sequence similarity. Besides manually, the sequences can be optimally aligned for the comparison by means of the local homology algorithm of Smith and Waterman (1981) (Ad. App. Math. 2: 482), by means of the local homology algorithm of Neddleman and Wunsch (1970) (J. Mol. Biol. 48: 443), by means of the homology search method of Pearson and Lipman (1988) (Proc. Natl. Acad. Sci. USA 85: 2444), by means of computer software running said algorithms (GAP, BESTFIT, FASTA and TFASTA in the Wisconsin Genetics Software Package, Genetics Computer Group, 575 Science Dr., Madison, Wis.). The percent identity between two nucleic acid or amino acid sequences is determined by comparing these two optimally aligned sequences by windows of comparison in which the region of nucleic acid or amino acid sequence to be compared may comprise additions or deletions relative to the reference sequence for an optimal alignment between these two sequences. The percent identity is calculated by determining the number of identical positions for which the nucleotide or amino acid residue is identical between the two sequences, by dividing said number of identical positions by the total number of positions in the comparison window and by multiplying the result by 100 in order to obtain the percent identity between these two sequences.

DETAILED DESCRIPTION OF THE INVENTION

The present invention therefore describes for the first time the genes encoding the enzymes involved in the synthetic pathway of many sesquiterpenes. In particular, the present invention relates to the characterization of a tomato sesquiterpene synthase with multiple products (SB synthase) which enables the production of a mixture of sesquiterpenes referred to as SB type compounds and composed mainly of alpha-santalene, epi-beta-santalene, cis-alpha -bergamotene,trans-alpha-bergamotene and endo-beta-bergamotene, from ZZ-FPP. In addition, the invention further relates to the characterization of Z,Z-farnesyl diphosphate synthase (zFPS) of tomato which enables the production of Z,Z-FPP from IPP and DMAPP. These enzymes can be used to produce SB type sesquiterpenes or Z,Z-FPP, in vitro or in vivo in transgenic organisms or recombinant microorganisms or cells. Transgenic organisms, cells or microorganisms such as bacteria, yeasts, fungi, animal, insect or plant cells and transgenic animals or plants are considered. They also enable the production of compounds derived from Z,Z-FPP such as ZZ-farnesol. The methods of the present invention can be used more particularly for producing Z,Z-FPP in microorganisms (bacteria, yeasts), and SB type compounds in plants possessing glandular trichomes of secretory type. The production of the SB type sesquiterpene mixture or derivatives thereof can also be reduced or suppressed in plants, for example tomato, by gene extinction techniques or by mutagenesis. In addition, the sequences identified in the present invention are useful for identifying and/or cloning genes encoding enzymes having the same activities in other species of organisms, in particular plants. Finally, polymorphic molecular markers can be identified from the nucleic acids encoding zFPS and SB synthase and will make it possible to monitor the introduction of the corresponding functional genomic sequences into other species or varieties of cultivated tomato (*Solanum lycopersicum*).

Z,Z-FPP is a potential substrate of sesquiterpene synthases but currently it is not commercially available. Although the majority of sesquiterpene synthases characterized to date use E,E-FPP, it is also clear that the lack of commercially available Z,Z-FPP has greatly limited its use for experimental purposes. Cotton cadinene synthase is the only example that describes the preferential use of Z,Z-FPP by a sesquiterpene synthase (Heinstein et al., 1970). In this case Z,Z-FPP was produced by chemical synthesis, and the Z,Z-FPP synthase described in this patent provides a method for producing said molecule in an easy and inexpensive manner.

Furthermore, SB type sesquiterpenes contain alpha-santalene, itself the direct precursor of alpha-santalol. Alpha-santolol is one of the characteristic constituents of sandalwood oil. Sandalwood oil is highly valued in the perfume industry and its prices have risen sharply over the past 10 years due to the overexploitation of sandalwood, primarily in India. This overexploitation poses a threat to the viability of natural sandalwood resources. Alpha-santolol can be obtained from alpha-santalene by a simple hydroxylation.

The present invention therefore relates to a method for producing SB type sesquiterpenes or derivatives thereof from Z,Z-FPP in a cell having a source of DMAPP and IPPP, comprising:
  a) introducing into said cell a construct having an expression cassette comprising a first gene encoding a zFPS according to the present invention and a construct having an expression cassette comprising a second gene encoding a SB synthase according to the present invention;
  b) culturing the transformed cell in suitable conditions for the expression of said first and said second genes; and,
  c) optionally, collecting the SB type sesquiterpenes or derivatives thereof contained in said cell and/or in the culture medium.

In a particular embodiment, the produced SB type sesquiterpenes are collected in step c). In a preferred embodiment, the SB type sesquiterpenes that are produced are selected in the group consisting of alpha-santalene, epi-beta-santalene, alpha-bergamotene, beta-bergamotene, and endo-beta-bergamotene. In another particular embodiment, the produced SB type sesquiterpenes are starting products to obtain other compounds of interest such as alpha-santalol. In a preferred embodiment, the SB type sesquiterpene derivatives are selected from the group consisting of alpha-santalol, epi-beta-santalol, cis-alpha-bergamotol, trans-alpha-bergamotol and endo-beta-bergamotol.

In a particular embodiment, the present invention relates to a method for producing SB type sesquiterpenes or derivatives thereof from Z,Z-FPP in a cell having a source of DMAPP and IPPP, comprising:
  a) providing a recombinant cell comprising a first heterologous gene encoding a zFPS according to the present invention and a second heterologous gene encoding a SB synthase according to the present invention;
  b) culturing said cell in suitable conditions for the expression of said first and said second genes; and,
  c) optionally, collecting the SB type sesquiterpenes or derivatives thereof contained in said cell and/or in the culture medium.

In a preferred embodiment, said cell produces Z,Z-FPP. In another embodiment, Z,Z-FPP is supplied to the cell.

In a particular embodiment, the two expression cassettes are carried by a same construct. In another embodiment, the two expression cassettes are carried by two separate constructs.

The present invention relates to an isolated or recombinant protein having Z,Z-FPP synthase activity. In particular, the invention relates to an isolated or recombinant polypeptide having Z,Z-FPP synthase activity and having sequence with at least 80%, 85%, 90%, 95%, 97%, 98% or 99% identity to SEQ ID No. 2. Preferably, the polypeptide has a sequence with at least 95% identity to SEQ ID No. 2. In a particular embodiment, the peptide comprises or consists of the sequence SEQ ID No. 2. Said polypeptide can also comprise an additional sequence facilitating the purification of the enzyme, for example a tag sequence comprising several consecutive histidine amino acids.

The present invention also relates to an isolated nucleic acid comprising a nucleotide sequence encoding a polypeptide having Z,Z-FPP synthase activity and having sequence with at least 80%, 85%, 90%, 95%, 97%, 98% or 99% identity to SEQ ID No. 2 or a sequence capable of hybridizing thereto in stringent conditions. An example of a nucleic acid is a nucleic acid comprising or consisting of a sequence with at least 80%, 85%, 90%, 95%, 97%, 98% or 99% identity to SEQ ID No. 1 or a complementary sequence thereof. The present invention relates to an isolated nucleic acid capable of hybridizing in conditions of high stringency to a nucleic acid encoding a polypeptide having Z,Z-FPP synthase activity and said polypeptide having sequence with at least 95% or 98% identity to SEQ ID No. 2. In a particular embodiment, the nucleic acid comprises or consists of the sequence SEQ ID No. 1. The present invention also relates to an expression cassette, a vector, a host cell or a transgenic organism comprising a nucleic acid according to the invention.

The nucleic acids can be genomic DNA, complementary DNA (cDNA) or synthetic DNA. Nucleic acids can be in single stranded or duplex form or a mixture of the two. In the present invention, the transcribed nucleic acids are preferably intronless cDNA. The transcribed nucleic acids can be synthetic or semisynthetic, recombinant molecules, optionally amplified or cloned into vectors, chemically modified or comprising non-natural bases. Typically they are isolated DNA molecules, synthesized by recombinant techniques well known to one skilled in the art.

The present invention also relates to an isolated or recombinant polypeptide having SB synthase activity and having sequence with at least 80%, 85%, 90%, 95%, 97%, 98% or 99% identity to SEQ ID No. 4. In a particular embodiment, the polypeptide comprises or consists of the sequence SEQ ID No. 4. In this case, the present invention relates to an isolated or recombinant polypeptide having SB synthase activity and having sequence with at least 95% identity to SEQ ID No. 4. Said polypeptide can also comprise an additional sequence facilitating purification of the enzyme, for example a tag sequence comprising several consecutive histidine amino acids.

The present invention also relates to an isolated nucleic acid comprising a nucleotide sequence encoding a polypeptide having SB synthase activity and having at least 80%, 85%, 90%, 95%, 97%, 98% or 99% identity to SEQ ID No. 4 or a sequence capable of hybridizing thereto in stringent conditions. An example of such nucleic acid is a nucleic acid comprising or consisting of a sequence with at least 80%, 85%, 90%, 95%, 97%, 98% or 99% identity to SEQ ID No. 3 or a complementary sequence thereof. The present invention relates to an isolated nucleic acid capable of hybridizing in conditions of high stringency to a nucleic acid encoding a polypeptide having SB synthase activity and said polypeptide having sequence with at least 95% or 98% identity to SEQ ID No. 4. In a particular embodiment, the nucleic acid comprises or consists of the sequence SEQ ID No. 3. The present invention also relates to an expression cassette, a vector, a host cell or a transgenic organism comprising a nucleic acid according to the invention.

The present invention more particularly relates to a vector, a host cell or a transgenic organism comprising a nucleic acid comprising a heterologous sequence encoding a polypeptide having SB synthase activity and having sequence with at least 80%, 85%, 90%, 95%, 97%, 98% or 99% identity to SEQ ID No. 4 and a nucleic acid comprising a heterologous sequence encoding a polypeptide having Z,Z-FPP synthase activity and having sequence with at least 80%, 85%, 90%, 95%, 97%, 98% or 99% identity to SEQ ID No. 2. In a particular embodiment of the invention, the transgenic organism is a plant, and in particular a plant trichomes.

The present invention also relates to a vector, a host cell or a transgenic organism comprising a nucleic acid comprising a heterologous sequence encoding a polypeptide having SB synthase activity and having sequence with at least 80%, 85%, 90%, 95%, 97%, 98% or 99% identity to SEQ ID No. 4.

The present invention also relates to a vector, a host cell or a transgenic organism comprising a nucleic acid comprising a heterologous sequence encoding a polypeptide having Z,Z-FPP synthase activity, preferably having sequence with at least 80%, 85%, 90%, 95%, 97%, 98% or 99% identity to SEQ ID No. 2.

The present invention relates to a method for producing a SB type sesquiterpenes mixture or derivatives thereof from IPP and DMAPP comprising contacting IPP and DMAPP with a purified or recombinant Z,Z-FPP synthase with at least 80%, 85%, 90%, 95%, 97%, 98% or 99% identity to SEQ ID No. 3 and a purified or recombinant SB synthase with at least 80%, 85%, 90%, 95%, 97%, 98% or 99% identity to SEQ ID No. 4 in suitable conditions and collecting an obtained SB type sesquiterpenes mixture or derivatives thereof. The invention relates to the use of a purified or recombinant Z,Z-FPP synthase with at least 80%, 85%, 90%, 95%, 97%, 98% or 99% identity to SEQ ID No. 2 and a purified or recombinant SB synthase with at least 80%, 85%, 90%, 95%, 97%, 98% or 99% identity to SEQ ID No. 4 for preparing a SB type sesquiterpenes mixture or derivatives thereof from IPP and DMAPP.

The present invention relates to a method for producing Z,Z-FPP or derivatives thereof from IPP and DMAPP comprising contacting IPP and DMAPP with a purified or recombinant Z,Z-FPP synthase with at least 80%, 85%, 90%, 95%, 97%, 98% or 99% identity to SEQ ID No. 2 in suitable conditions and collecting the obtained Z,Z-FPP or derivatives thereof. Optionally, the method further comprises incubating Z,Z-FPP obtained with a calf intestine alkaline phosphatase and collecting Z,Z-farnesol. The present invention relates to the use of a purified or recombinant Z,Z-FPP synthase with at least 80%, 85%, 90%, 95%, 97%, 98% or 99% identity to SEQ ID No. 2 for preparing Z,Z-FPP or derivatives thereof from IPP and DMAPP.

The present invention relates to a method for producing Z,Z-FPP or derivatives thereof from IPP and DMAP comprising contacting IPP and DMAP with a purified or recombinant Z,Z-FPP synthase with at least 80%, 85%, 90%, 95%, 97%, 98% or 99% identity to SEQ ID No. 2 in suitable conditions and collecting the obtained Z,Z-FPP or derivatives thereof. Optionally, the method further comprises incubating Z,Z-FPP obtained with a calf intestine alkaline phosphatase and collecting Z,Z-farnesol. The present invention relates to the use of a purified or recombinant Z,Z-FPP synthase with at least 80%, 85%, 90%, 95%, 97%, 98% or 99% identity to SEQ ID No. 2 for preparing Z,Z-FPP or derivatives thereof from IPP and DMAP.

The present invention relates to a method for producing a mixture of class II sesquiterpenes or derivatives thereof from Z,Z-FPP comprising contacting Z,Z-FPP with a purified or recombinant SB synthase with at least 80%, 85%, 90%, 95%, 97%, 98% or 99% identity to SEQ ID No. 4 in suitable conditions and collecting a obtained SB type sesquiterpenes mixture or derivatives thereof. The invention relates to the use of a purified or recombinant SB synthase with at least 80%, 85%, 90%, 95%, 97%, 98% or 99% identity to SEQ ID No. 4 for preparing a mixture of class II sesquiterpenes or derivatives thereof from Z,Z-FPP.

Generally, an expression cassette comprises all the elements required for gene transcription and translation into a protein. In particular, it comprises a promoter, optionally an enhancer, a transcription terminator and the elements for translation.

The promoter is adapted to the host cell. For example, if the cell is prokaryotic, the promoter can be selected from the group consisting of the following promoters: LacI, LacZ, pLacT, ptac, pARA, pBAD, the RNA polymerase promoters of bacteriophage T3 or T7, the polyhedrin promoter, the PR or PL promoter of lambda phage. If the cell is eukaryotic and animal, the promoter can be selected from the group consisting of the following promoters: cytomegalovirus (CMV) early promoter, herpes simplex virus (HSV) thymidine kinase promoter, simian 40 virus (SV40) early or late promoter, mouse metallothionein-L promoter, and the LTR (long terminal repeat) regions of certain retroviruses. Generally, to choose a suitable promoter, one skilled in the art can advantageously refer to the work of Sambrook and Russell (2000) or else to the methods described in the work of Ausubel et al. (2006).

The vector can be a plasmid, a phage, a phagemid, a cosmid, a virus, a YAC, a BAC, an *Agrobacterium* pTi plasmid, etc. The vector can preferably comprise one or more elements selected from a replication origin, a multiple cloning site and a marker. The marker can be a reporter gene which produces a detectable signal. The detectable signal can be a fluorescent signal, a staining, a light emission. The marker can therefore be GFP, EGFP, DsRed, beta-galactosidase, beta-glucosidase, luciferase, etc. The marker is preferably a selection marker which confers antibiotic or herbicide resistance to the cell. For example, the gene can be a kanamycin, neomycin, etc. resistance gene. In a preferred embodiment, the vector is a plasmid. Examples of prokaryotic vectors include, but are not limited to, the following: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pBR322, and pRIT5 (Pharmacia), pET (Novagen) and pQE-30 (QIAGEN). Examples of eukaryotic vectors include, but are not limited to, the following: pWLNEO, pSV2CAT, pPICZ, pcDNA3.1 (+) Hyg (Invitrogen), pOG44, pXT1, pSG (Stratagene); pSVK3, pBPV, pCI-neo (Stratagene), pMSG, pSVL (Pharmacia). Viral vectors include, but are not limited to, adenoviruses, AAV, HSV, lentiviruses, etc. Preferably, the expression vector is a plasmid or a viral vector.

The host cell can be a prokaryote, for example *Escherichia coli, Bacillus subtilis, Streptomyces* sp, and *Pseudomonas* sp or a eukaryote. The eukaryote can be a lower eukaryote such as a yeast (for example, *Saccharomyces cerevisiae*) or filamentous fungus (for example from the genus *Aspergillus*) or a higher eukaryote such as an insect, mammalian or plant cell. The cell can be a mammalian cell, for example a COS, CHO cell (U.S. Pat. Nos. 4,889,803; 5,047,335). In a particular embodiment, the cell is non-human and non-embryonic. The cell can be isolated, for example in a culture medium. The cells can also be comprised in organisms, for example non-human transgenic animals or transgenic plants.

The present invention therefore relates to a method for producing Z,Z-FPP or derivatives thereof from IPP and DMAPP in a cell having an IPP and DMAPP source, comprising:
 a) introducing into said cell a construct having an expression cassette comprising a gene encoding a Z,Z-FPP synthase according to the present invention;
 b) culturing the transformed cell in suitable conditions for the expression of the gene; and,
 c) optionally, collecting the Z,Z-FPP or derivatives thereof contained in said cell and/or in the culture medium.

In a particular embodiment, the Z,Z-FPP produced is collected in step c). In another particular embodiment, the Z,Z-FPP produced is the starting product to obtain another compound of interest such as Z,Z-farnesol. For example, Z,Z-FPP can be converted to Z,Z-farnesol by a phosphatase. Thus, the method can further comprise at step a) the introduction of a construct having an expression cassette comprising a gene encoding a phosphatase, thereby allowing Z,Z-farnesol to be collected in step c). The present invention therefore relates to a method for producing Z,Z-FPP or derivatives thereof from IPP and DMAPP in a recombinant cell having an IPP and DMAPP source and comprising a heterologous gene encoding a Z,Z-FPP synthase according to the present invention.

The present invention thus relates to a method for producing Z,Z-FPP in a recombinant cell having a IPPP and DMAPP source, comprising:
 a) providing a recombinant cell comprising a heterologous gene encoding a zFPS according to the present invention;
 b) culturing the cell in suitable conditions for the expression of said gene; and,
 c) optionally, collecting the Z,Z-FPP or derivatives thereof contained in said cell and/or in the culture medium.

The present invention therefore relates to a method for producing a SB type sesquiterpenes mixture or derivatives thereof from Z,Z-FPP in a cell having a Z,Z-FPP source, comprising:
 a) introducing into said cell a construct having an expression cassette comprising a gene encoding a SB synthase according to present invention;
 b) culturing the transformed cell in suitable conditions for the expression of the gene; and,
 c) optionally, collecting a SB type sesquiterpenes mixture or derivatives thereof contained in said cell and/or in the culture medium.

In a particular embodiment, the produced SB type sesquiterpene mixture is collected in step c). In another particular embodiment, the SB type sesquiterpene mixture produced is the starting product to obtain another compound of interest such as alpha-santalol. The present invention therefore relates to a method for producing a SB type sesquiterpenes mixture or derivatives thereof from Z,Z-FPP in a recombinant cell having a Z,Z-FPP source and comprising a heterologous gene encoding a SB synthase according to the present invention. The present invention thus relates to a method for producing SB type sesquiterpenes or derivatives thereof from Z,Z-FPP in a recombinant cell having a Z,Z-FPP source, comprising:
 a) providing a recombinant cell comprising a heterologous gene encoding a SB synthase according to the present invention;
 b) culturing the cell in suitable conditions for the expression of said gene; and,
 c) optionally, collecting a SB type sesquiterpenes mixture or derivatives thereof contained in said cell and/or in the culture medium.

The cells can also be part of a multicellular organism, for example a plant or a non-human animal. In this case, the present invention relates to a method for preparing a multicellular organism comprising:
 a) introducing into a cell of the organism a construct having an expression cassette comprising a first gene encoding a Z,Z-FPP synthase according to the invention and a construct having an expression cassette comprising a second gene encoding a SB synthase according to the invention; and,
 b) reconstituting an organism from said cell and selecting the transgenic organisms expressing the two genes that were introduced.

In one embodiment, the organism is a non-human animal. For example, the organism can be a mouse, rat, guinea pig, rabbit, etc. In another preferred embodiment, the organism is a plant, preferably a plant glandular trichomes.

The present invention therefore relates to a method for producing a SB type sesquiterpenes mixture comprising providing a transgenic multicellular organism expressing a Z,Z-FPP synthase according to the present invention and a SB synthase according to the present invention and collecting a SB type sesquiterpenes mixture or derivatives thereof in said transgenic organisms.

The method makes it possible to produce a SB type sesquiterpenes mixture in organisms which do not produce such compounds or to increase the amount of a SB type sesquiterpene mixture produced by organisms which already produce it.

The present invention therefore relates to a method for preparing a multicellular organism comprising:
 a) introducing into a cell of the organism a construct having an expression cassette comprising a gene encoding a Z,Z-FPP synthase according to the present invention; and
 b) reconstituting an organism from said cell and selecting the transgenic organisms expressing the introduced gene.

The present invention also relates to a method for producing Z,Z-FPP or derivatives thereof comprising providing a transgenic multicellular organism expressing a Z,Z-FPP synthase according to the present invention and collecting the produced Z,Z-FPP or derivatives thereof in said transgenic organisms.

In one embodiment, the organism is a non-human animal. For example, the organism can be a mouse, rat, guinea pig, rabbit, etc. In another preferred embodiment, the organism is a plant, preferably a plant having glandular trichomes. The method makes it possible to produce Z,Z-FPP in organisms which do not produce said compound or to increase the amount of Z,Z-FPP produced by the organisms.

The present invention therefore relates to a method for preparing a multicellular organism comprising:
a) introducing into a cell of the organism a construct having an expression cassette comprising a gene encoding a SB synthase according to the present invention; and
b) reconstituting an organism from said cell and selecting the transgenic organisms expressing the introduced gene.

The present invention also relates to a method for producing a SB type sesquiterpenes mixture or derivatives thereof comprising providing a transgenic multicellular organism expressing a SB synthase according to the present invention and collecting a produced SB type sesquiterpenes mixture or derivatives thereof in said transgenic organisms. In one embodiment, the organism is a non-human animal. For example, the organism can be a mouse, rat, guinea pig, rabbit, etc. In another preferred embodiment, the organism is a plant, preferably a plant secretory trichomes. The method makes it possible to produce a SB type sesquiterpenes mixture by organisms which do not produce said compounds or to increase the amount of a SB type sesquiterpene mixture produced by the organisms.

In particular, the invention is applicable to all plants from families with glandular trichomes, for example Asteraceae (sunflower, etc.), Solanaceae (tomato, tobacco, potato, pepper, eggplant, etc.), Cannabaceae *Cannabis sativa*) and Lamiaceae (mint, basil, lavender, thyme, etc.). The invention is particularly adapted to plants of the Solanaceae family, such as for example from the genera *Nicotiana, Solanum, Capsicum, Petunia, Datura, Atropa*, etc., and in particular the genera *Solanum* and *Nicotiana* such as for example the cultivated tomato (*Solanum lycopersicum*), the wild tomato *Solanum habrochaites*, cultivated tobacco (*Nicotiana tabacum*), woodland tobacco (*Nicotiana sylvestris*). In a non-limiting manner, the invention can apply to plants from the following genera: *Populus, Nicotiana, Cannabis, Pharbitis, Apteria, Psychotria, Mercurialis, Chrysanthemum, Polypodium, Pelargonium, Mimulus, Matricaria, Monarda, Solanum, Achillea, Valeriana, Ocimum, Medicago, Aesculus, Plumbago, Pityrogramma, Phacelia, Avicennia, Tamarix, Frankenia, Limonium, Foeniculum, Thymus, Salvia, Kadsura, Beyeria, Humulus, Mentha, Artemisia, Nepta, Geraea, Pogostemon, Majorana, Cleome, Cnicus, Parthenium, Ricinocarpos, Hymennaea, Larrea, Primula, Phacelia, Dryopteris, Plectranthus, Cypripedium, Petunia, Datura, Mucuna, Ricinus, Hypericum, Myoporum, Acacia, Diplopeltis, Dodonaea, Halgania, Cyanostegia, Prostanthera, Anthocercis, Olearia, Viscaria*. Preferably, the plant is a plant from the Asteraceae, Cannabaceae, Solanaceae or Lamiaceae family. In a more preferred embodiment, the plant belongs to the genera *Solanum* or *Nicotiana*, preferably *Solanum esculentum, Solanum habrochaites, Nicotiana tabacum* or *Nicotiana sylvestris*.

In this embodiment, the genes are under the control of a promoter allowing an expression, preferably specific, in the trichomes of the plant. Such promoters exist and are known to one skilled in the art (Tissier et al., 2004).

In the invention, "specific" promoter refers to a promoter which is active mainly in a given tissue or cell group. It shall be understood that a residual expression, generally lower, in other tissues or cells cannot be entirely ruled out. A particular feature of the invention is based on the ability to construct promoters specific for the secretory cells of glandular trichomes, allowing a modification of the composition of the plant foliary secretions, and in particular to express therein the genes of the present invention allowing the preparing of a SB type sesquiterpenes mixture. Thus, Z,Z-FPP, and the SB type sesquiterpenes mixture or derivatives thereof can be collected from the trichomes of said plants, in particular in the trichome exudate, by extraction with a solvent or else by distillation.

For example, it has been shown that a 1852 by regulatory sequence, located upstream the ATG of the CYP71D16 gene, directs the expression of the uidA reporter gene specifically in the secretory cells of tobacco trichomes (application US2003/0100050 A1, Wagner et al., 2003). Moreover, several promoter sequences extracted from different species have been identified as being able to direct the expression of a heterologous gene in tobacco trichomes.

| Gene Abbreviation | Name of gene | Plant | References |
|---|---|---|---|
| LTP3 | Lipid transfer protein | Cotton | Liu et al., 2000, BBA, 1487: 106111 |
| LTP6 | | Cotton | Hsu et al., 1999, Plant Science, 143: 6370 |
| wax9D | | B. oleracea | Pyee and Kolattukudy, 1995, Plant J. 7: 4559 |
| LTP1 | | Arabidopsis | Thoma et al., 1994, Plant Physiol. 105 3545 |
| CYC71D16 | CBTol hydroxylase | Tobacco | Wang et al., 2002, J. Exp. Bot. 18911897 |

In a preferred embodiment of the present invention, the promoter used in the cassette is derived from the genes NsTPS-02a, 02b, 03, and 04 of the *Nicotiana sylvestris* species showing a strong sequence similarity with CYC-2 (CBTol cyclase; NID: AF401234). Said promoter sequences are more fully described in patent application WO2006040479 (Tissier et al., 2004).

Among the preferred terminator sequences, the NOS terminator (Bevan et al., 1983), and the histone gene terminator (EPO 633 317) may be mentioned.

In a particular embodiment, the expression cassette can comprise a sequence allowing to increase expression ("enhancer"), for example certain elements of the CaMV35S promoter and octopine synthase genes (U.S. Pat. No. 5,290,924). Preferably, the enhancer elements of the CaMV35S promoter are used.

The introduction of constructs having one or both genes of the invention into a cell or a plant tissue, including a seed or plant, can be carried out by any method known to one skilled in the art, including in episomal or chromosomal form. Plant transgenesis techniques are well known in the field, and comprise for example the use of the bacteria *Agrobacterium tumefaciens*, electroporation, gene gun techniques, transfection by a viral vector in particular, and any other method known to one skilled in the art.

One commonly used method, based on the use of the bacterium *Agrobacterium tumefaciens*, consists mainly in introducing the construct of interest (nucleic acid, cassette, vector, etc.) into the bacterium *A. tumefaciens*, then contacting this transformed bacterium with leaf discs of the chosen plant.

The expression cassette is typically introduced into the bacteria by using as vector the Ti plasmid (or T-DNA), which can be transferred into the bacteria for example by heat shock or by electroporation. Incubation of the transformed bacterium with the leaf discs results in transfer of the Ti plasmid into the genome of disc cells. These can optionally be cultivated in suitable conditions in order to reconstitute a transgenic plant whose cells comprise the construct of the invention. For further details or for variant implementations of the *A. tumefaciens* transformation technique, one may refer for example to Horsch et al. (1985) or to Hooykaas and Schilperoort (1992).

Thus, in a particular embodiment, the expression cassette so constituted is inserted between the left and right borders of transfer DNA (T-DNA) of a disarmed Ti plasmid for transfer into plant cells by *Agrobacterium tumefaciens*. The T-DNA also comprises a gene which expression confers a resistance to an antibiotic or herbicide and which enables the selection of transformants.

Once regenerated, transgenic plants can be tested for heterologous expression of the genes of the present invention or the production of a SB type sesquiterpenes mixture, Z,Z-FPP or Z,Z-farnesol in the trichomes. This can be achieved by collecting the leaf exudate and testing for the presence of the product of interest in said exudate. Analysis of volatile compounds emitted by the plant can also allow identification of said compounds. This can also be done by analyzing the presence of one or more heterologous enzymes of the present invention in the leaves and, more particularly, in the trichome cells (for example by analyzing mRNA or genomic DNA with specific primers or probes). The plants can optionally be selected, crossed, treated, etc. in order to obtain plants having improved expression levels.

Another object of the invention is also based on a plant or seed comprising a nucleic acid, an expression cassette or a vector such as defined hereinabove.

A further object of the invention relates to the use of a nucleic acid of the present invention as molecular markers to enable the introduction of the corresponding genomic sequences of *S. habrochaites* into other sexually compatible species or varieties of cultivated tomato (*S. lycopersicum*). In fact, said markers make it possible to control the introduction of the corresponding genomic sequences of *S. habrochaites* into other sexually compatible species or varieties of cultivated tomato (*S. lycopersicum*) and thus, for example, to identify and select individuals produced from a cross between the wild species and a cultivated species in which the introgression of nucleic acids of the present invention has taken place. The use of the nucleic acids of the present invention as molecular markers can be carried out by any technique known to one skilled in the art. For example, a commonly used technique is based on identifying a band polymorphism (RFLP) between two genomes digested by different restriction enzymes by molecular hybridization with the nucleic acids of the present invention. Another example is to search for a polymorphism by using PCR to amplify, on the genomes to be compared, all or part of a nucleic acid of the present invention from primers complementary to the nucleic acid of the present invention in order to identify, after PCR amplification, a size polymorphism between the two genomes. The polymorphism can also be revealed after digestion of said PCR products by one or more restriction enzymes which produce fragments of different size between the compared genomes.

Once the polymorphism is identified, this information is used, for example, to identify individuals in an F2 population derived from a cross between *S. habrochaites* and a variety of tomato in which the introgression of the nucleic acids of the present invention is desired.

Another object of the invention relates to the introduction of genomic sequences of *S. habrochaites* encoding zFPS and SB synthase into non-sexually compatible species by fusion of cells, in particular of protoplasts. Protoplast fusion techniques are known to one skilled in the art (Zimmermann et al., 1981, Bates et al., 1983), and make it possible to create hybrid cells containing chromosomes belonging to the two fused species. During fusion chromosomes or chromosome fragments of the two species are eliminated. Hybrid cells having retained the chromosomal fragment(s) containing the genes of the present invention can then be selected by PCR using primers specific of the gene encoding zFPS (SEQ ID No. 1) or that encoding SB synthase (SEQ ID No. 2) or both at once.

The present invention also relates to a cell or a non-human transgenic organism, characterized in that the synthetic pathway of a SB type sesquiterpene mixture is blocked by inactivation of the gene encoding a Z,Z-FPP synthase according to the present invention or the gene encoding a SB synthase according to the present invention or both genes. The expression of said genes can be blocked by many available techniques known to one skilled in the art. The genes can be deleted, mutated (for example, by chemical mutagenesis with Ethyl Methane Sulfonate or by ionizing irradiation) or interrupted (insertional mutagenesis). Moreover, the expression of said genes can also be blocked by gene extinction by expressing an inhibitory transcript. The inhibitory transcript is an RNA which can be in the form of a double-stranded RNA, an antisense RNA, a ribozyme, an RNA able to form a triple helix, and which has some complementarity or specificity with the transcript of the gene to be blocked.

The present invention also relates to a nucleic acid that can reduce or suppress the expression of a gene encoding a Z,Z-FPP synthase. In fact, an inhibitor RNA which can be in the form of a double-stranded RNA, an antisense RNA, a ribozyme, an RNA able to form a triple helix, and which has some complementarity or specificity with the gene encoding Z,Z-FPP synthase, can be prepared on the basis of the teachings of the present invention. For instance, the present invention relates to an inhibitor RNA of the gene encoding a Z,Z-FPP synthase comprising at least 21, 30, 40, 50, 60, 70, 80, 90 or 100 consecutive nucleotides of SEQ ID No. 1 or of a complementary sequence thereto. Likewise, the invention relates to the use of a polynucleotide comprising at least 21, 30, 40, 50, 60, 70, 80, 90 or 100 consecutive nucleotides of SEQ ID No. 1 or of a complementary sequence thereto for inhibiting the expression of the gene encoding a Z,Z-FPP synthase Inhibition of this enzyme can be useful for stopping or slowing down the synthetic pathway of the SB type sesquiterpene mixture and making IPP and DMAPP available for another synthetic pathway of interest requiring a supply of Z,Z-FPP. For example, inhibition of this enzyme can lead to an increase in the production level of germacrene B by tomato leaf glandular trichome cells. The present invention therefore relates to transgenic organisms or cells in which the gene encoding a Z,Z-FPP synthase has been inactivated. The inactivation can be achieved by techniques of RNA interference, gene deletion, chemical mutation or inactivation by homologous recombination. Thus the content of Z,Z-FPP or of SB type sesquiterpene mixture can be reduced in said transgenic organisms or cells.

Furthermore, the present invention also relates to a nucleic acid that can reduce or suppress the expression of a gene encoding a SB synthase. Indeed, an inhibitor RNA which can be in the form of a double-stranded RNA, an antisense RNA, a ribozyme, an RNA able to form a triple helix, and which has some complementarity or specificity with the gene encoding a SB synthase, can be prepared on the basis of the teachings of the present invention. Thus, the present invention relates to an inhibitor RNA of the gene encoding a SB synthase comprising at least 30, 40, 50, 60, 70, 80, 90 or 100 consecutive nucleotides of SEQ ID No. 3. Likewise, the invention relates to the use of a polynucleotide comprising at least 21, 30, 40, 50, 60, 70, 80, 90 or 100 consecutive nucleotides of SEQ ID No. 3 in order to inhibit the expression of the gene encoding a SB synthase. The inhibition of this enzyme can be useful for stopping the synthetic pathway of a SB type sesquiterpene mixture and making Z,Z-FPP available for another synthetic pathway of interest requiring a supply of said compound, for example for preparing Z,Z-FPP derivatives, for example, Z,Z farnesol, or other sesquiterpenes which are the product of synthases that use Z,Z-FPP as substrate.

The present invention therefore relates to cells or transgenic organisms in which the gene encoding a SB synthase is inactivated. The inactivation can be achieved by RNA interference techniques, gene deletion, chemical mutation or inactivation by homologous recombination. Thus, the content of SB type sesquiterpene mixture can be reduced in said cells or transgenic organisms.

The present invention also relates to a method for identifying or cloning other genes encoding a Z,Z-FPP synthase or a SB synthase originating from another species in which a probe having at least 15, 30, 50, 75, 100, 200 or 300 consecutive nucleotides of sequence SEQ ID No. 1 or 3, respectively, is prepared and used to identify or select in a sample a nucleotide sequence capable of hybridizing with said probe. The sample can be for example a genomic or cDNA library originating from one or more organisms. The method can comprise an additional step of characterizing the identified or selected sequence. This additional step can comprise cloning, and/or sequencing, and/or sequence alignment, and/or a test of enzymatic activity.

Other aspects and advantages of the present invention will become apparent in the following examples, which are given for purposes of illustration and not by way of limitation.

EXAMPLES

Synthesis of tomato leaf cDNA (*S. habrochaites*)

mRNA was extracted from tomato leaf (*Solanum habrochaites=L. Hirsutum* LA1777) using a total RNA extraction kit (RNeasy Minikit, Qiagen). The corresponding cDNA was synthesized by reverse transcription from a polyT primer by using reverse transcriptase (Roche, Cat. No. 03 531 317) in the reaction conditions recommended by the manufacturer.

Cloning of coding sequences for Z,Z-FPP synthase (Sh-zFPS) and SB synthase (Sh-SBS) from *Solanum habrochaites* tomato.

The complete and coding nucleotide sequence of the two genes Sh-zFPS and Sh-SBS were cloned from the publicly available sequence data in the EST library of *S. habrochaites* tomato leaf trichomes (Van der Hoeven, et al., 2000, unpublished,) available on the SGN website ("SOL Genomics Network", See Worldwide Website: Sgn.cornell.edu/).

The Sh-zFPS (SEQ ID No. 1) and Sh-SBS (SEQ ID No. 3) sequences of were obtained by PCR from tomato leaf cDNA using the primers 5'-A CCATGGGTTCTTTGGTTCTTCAATGTTGGA-3' (SEQ ID No. 5) and 5'-ACTCGAGATATGTGTGT-CCACCAAAACGTCTATG-3' (SEQ ID No. 6) for sequence ID No. 1 and the primers 5'-TCCATGGTAGTTGG-CTATAGAAGCACAATCA-3' (SEQ ID No. 7) and 5'-T CTCGAGCATAAATTCAAATTGAGGGATTAATGA-3' (SEQ ID No. 8) for sequence ID No. 3. Restriction enzyme sites (NcoI and XhoI) were added at the 5' end of the primers to facilitate cloning the cDNA downstream a promoter. PCR amplification was carried out with 0.5 units Taq polymerase (Eurogentec) in the buffer supplied by the manufacturer. The PCR product was purified on a Qiaquick column (Qiagen) and cloned by ligation with T4 DNA ligase (NEB) into the pGEM-T cloning vector (Promega). Clones having the expected sequence were selected after complete sequencing of the inserts.

The Sh-zFPS nucleotide sequence (SEQ ID No. 1) is 912 bases long and codes for a protein of 303 amino acids (SEQ ID No. 2). A conserved protein domain of the type cis (Z)-isoprenyl diphosphate synthase (cis-IPPS) or also known as undecaprenyl synthase (UPPS) was identified "in silico" with the CCD system (NCBI, Marchler-Bauer A, Bryant SH (2004). Amino acid sequences similar to Sh-zFPS were searched in the SwissProt and GenBank protein data bases using BlastP software (Altschul et al., 1997). The highest percent identities were obtained with plant sequences showing homology to undecaprenyl diphosphate synthases but whose functions have not been demonstrated (Table 1). For example, Sh-zFPS has 42% and 39% identity, respectively, to the putative UPPS of *Arabidopis thaliana* BAA97345 and AAO63349. It can also be seen that the Sh-zFPS sequence has a very low percent identity (24%) to Z,E-FPS of *Micrococcus tuberculosis* (O53434).

TABLE 1

Sequences with the highest percent identity (% identity) obtained by homology search using BlastP 2.2.13 program (Altschul et al., 1997) against the SwissProt and GenBank libraries with the Sh-zFPS sequence.

| Organism | PID | Function | % identity |
|---|---|---|---|
| *Arabidopsis thaliana* | BAA97345 | Putative UPPS | 42 |
| *Arabidopsis thaliana* | AAO63349 | Putative UPPS | 39 |
| *Arabidopsis thaliana* | AAO42764 | Putative UPPS | 39 |
| *Anabaena* sp. PCC 7120 | DP58563 | Putative UPPS | 37 |
| *Oryza sativa* | NP_915561 | Putative UPPS | 36 |
| *Synechococcus elongatus* | Q8DI29 | Putative UPPS | 35 |
| *Micrococcus luteus* | O82827 | Putative UPPS | 34 |
| *Gloeobacer violaceus* | Q7NPE7 | Putative UPPS | 32 |
| *Micrococcus tuberculosis* | P60479 | UPPS | 30 |
| *Micrococcus tuberculosis* | O53434 | E,Z-FPS | 24 |

The Sh-SBS nucleotide sequence (SEQ ID No. 3) is 2334 bases long and codes for a protein of 777 amino acids (SEQ ID No. 4). A conserved terpene cyclase protein domain was identified "in silico" with the CCD system (NCBI, Marchler-Bauer A, Bryant S H (2004). Amino acid sequences similar to Sh-SBS were searched in the SwissProt and GenBank protein libraries using BlastP software (Altschul et al., 1997). With the exception of a tobacco sequence of unknown function (60% identity), the best homologies were obtained with plant diterpene synthases (Table 2) with approximately 40 to 45% identity to sequences encoding kaurene synthases of different plants (*Arabidopsis thaliana, Cucurbita maxima, Stevia rebaudiana, Oryza sativa*). Sh-SBS also shows less homology (26-33% identity) with terpene synthases of known function such as abietadiene synthase and taxadiene synthase and alpha-bisabolene synthase.

TABLE 2

Sequences with the highest percent identity (% identity) obtained by homology search using BlastP 2.2.13 program (Altschul et al., 1997) against the SwissProt and GenBank libraries with the Sh-SBS sequence.

| Organism | PID | Function | % identity |
|---|---|---|---|
| Nicotiana tabacum | AAS98912 | Putative terpene synthase | 60 |
| Arabidopsis thaliana | AAC39443 | Kaurene synthase | 44 |
| Lactuca sativa | BAB12441 | Putative kaurene synthase | 43 |
| Cucurbita maxima | Q39548 | Kaurene synthase | 43 |
| Medicago troncatula | ABE87878 | Putative terpene synthase | 43 |
| Stevia rebaudiana | AAD34294 | Kaurene synthase | 42 |
| Oryza sativa | AAQ72559 | Kaurene synthase | 41 |
| Hordeum vulgare | AAT49066 | Kaurene synthase | 36 |
| Abies grandis | AAC24192 | Alpha-bisabolene synthase | 33 |
| Abies grandis | AAB05407 | Abietadiene synthase | 27 |
| Taxus baccata | 2211347A | Taxadiene synthase | 26 |

Production of Sh-zFPS and Sh-SBS recombinant proteins

The nucleic sequences encoding Sh-zFPS and Sh-SBS (SEQ ID No. 1 and 3, respectively) were separately introduced into the pET-30b expression vector (Novagen). To allow purification of the recombinant proteins, the STOP codons of these sequences were deleted in order to create a fusion protein with a 6-histidine tail at the C-terminal end. The Sh-zFPS-pET30b and Sh-SBS-pET30b vectors so obtained were introduced by electroporation into *Escherichia coli* cells modified for expression of recombinant proteins (BL21-CodonPlus, Stratagene). To produce the proteins, *E. coli* cultures (500 ml) were initiated at 37° C. until reaching an optical density of 0.5 at 600 nm. At this stage, the culture temperature was lowered to 16° C. and ethanol (1% V/V) was added to the medium. After 1 h incubation, IPTG was added to the medium at 1 mM concentration to induce expression of the recombinant protein. The culture was then incubated for 18 h and stopped by centrifuging the cells at 4° C. The cell pellet was resuspended in 200 mM phosphate buffer. Cells were lysed with a French press ($\Delta P=19$ bar) and lysates were centrifuged at 15,000 g. Supernatants containing soluble proteins were desalted on a PD10 column (Amersham), equilibrated with 50 mM phosphate buffer, pH 7, and loaded on nickel-nitrilotriacetic affinity resin (Ni-NTA, Qiagen) in strict accordance with the manufacturer's elution protocol. The fractions with the highest amounts of Sh-zFPS-6His and Sh-SBS-6His proteins were identified by SDS-PAGE, then desalted on a PD10 column equilibrated with 50 mM HEPES buffer, pH 7.8, 100 mM KCl. An approximate 20-fold enrichment was obtained for the two proteins as compared to the crude protein fraction.

In vitro enzyme activity test of the Sh-zFPS and Sh-SBS recombinant proteins

Activity tests were carried out in the following buffer: 50 mM HEPES, pH 7.8, 100 mM KCl, 7.5 mM $MgCl_2$, 5% (w/v) glycerol, and 5 mM DTT. For the activity tests, 25 or 50 µg of protein from the enriched fraction were incubated for 2 h at 32° C. with the substrates IPP, DMAPP, GPP, FPP, GGPP (Sigma), alone or in combination, each at a concentration of 65 µM.

For tests carried out with Sh-zFPS-6His, the reaction products were dephosphorylated by addition of 20 units calf intestine alkaline phosphatase (New England Biolabs) for 1 h at 37° C. Terpene alcohols, which are phosphorylation products, were then extracted with a chloroform/methanol/water mixture (0.5/1/0.4). The aqueous and organic phases were separated by addition of water (0.5 vol) and chloroform (0.5 vol) and centrifuged at 2,000 g. The organic phases were collected and dried under a stream of nitrogen gas, taken up in pentane and analyzed by gas chromatography coupled with mass spectrometry (GC-MS 5973N, Agilent Technologies). The terpene alcohols were identified by comparing their mass spectra with those of the National Institute of Standards and Technology (NIST) data base, and by merging their retention times to those of geraniol, farnesol and geranylgeraniol reference standards (Fluka).

For tests carried out with Sh-SBS-6His, the terpenes produced in the reaction were directly extracted (three times) from the reaction mixture with pentane (volume-to-volume). The three pentane extracts were pooled, concentrated under a stream of nitrogen gas, and analyzed by GC-MS. The terpenes produced were identified by interrogating the NIST data base and comparison with a chromatogram of the extract of a *Solanum habrochaites* exudate.

The Sh-zFPS-6His recombinant protein was incubated with the substrates IPP+DMAPP or IPP+GPP (see Table 1). Only the first combination (IPP+DMAPP) led, after dephosphorylation, to the formation of a single terpene alcohol with 15 carbon atoms (C15), whose mass spectrum identified it as a farnesol by comparison with the standard spectrum in the NIST data base (FIG. 4). The retention time was compared to a farnesol standard containing a mixture of the four farnesol isomers (E,E-farnesol; E,Z-farnesol; Z,E farnesol and Z,Z-farnesol). The farnesol produced by Sh-zFPS-6His had a retention time identical to that of Z,Z-farnesol.

The Sh-SBS-6His recombinant protein was incubated with the substrates GPP, FPP and GGPP. Regardless of the substrate used, no new terpenes could be detected, indicating that the enzyme is inactive on trans-allylic substrates (Table 1).

TABLE 3

Summary of in vitro enzyme activity tests obtained on Sh-zFPS-6His and Sh-SBS-6His recombinant proteins with different isoprenoic substrates.

| Enz1 | Enz2 | Substrate | IPP | Products |
|---|---|---|---|---|
| Sh-zFPS | absent | DMAP | IPP | A* |
| Sh-zFPS | absent | E-GPP | IPP | — |
| absent | Sh-SBS | E-GPP | No | — |
| absent | Sh-SBS | E,E-FPP | No | — |
| absent | Sh-SBS | E,E,E-GGPP | No | — |
| Sh-zFPS | Sh-SBS | DMAPP | IPP | B, C, D, E, F |
| Sh-zFPS | Sh-SBS | GPP | IPP | — |

A, Z,Z-farnesol, B, alpha-santalene; C, epi-beta-santalene; D, endo-beta-bergamotene; E, cis-alpha-bergamotene; F, trans-alpha-bergamotene.
*after dephosphorylation The Sh-zFPS-6His and Sh-SBS-6His enzymes were incubated together with the substrates DMAPP and IPP or GPP and IPP. The reaction product was not treated with phosphatase, but extracted with pentane in which all olefins are soluble. With DMAPP and IPP as substrates, the chromatographic analysis of the extract revealed the presence of several terpene compounds (FIG. 5). The GC profile was compared with that of the exudate of the TA517 tomato line, a near isogenic line obtained from the parents *S. lycopersicum* and *S. habrochaites* (Monforte and Tanksley, 2000). The TA517 line contains an introgression fragment of *S. habrochaites* responsible for the biosynthesis of class II sesquiterpenes (van der Hoeven et al., 2000). The two GC profiles were identical, confirming that the recombinant enzymes have an activity strictly identical to those present in tomato (FIG. 6). The major component (FIG. 5, peak 2) was identified as alpha-santalene by comparing its retention time and mass spectrum with that of the TA517 exudate extract. In decreasing amounts, alpha-santalene (peak 4), endo-beta-bergamotene (peak 5), and alpha-bergamotene (peak 1) were also identified. The Sh-SBS-6His enzyme is therefore an enzyme whose activity leads to the formation of multiple products.

It may be concluded that Sh-zFPS is an enzyme that acts on IPP and DMAPP to produce a phosphorylated compound of farnesyl diphosphate type. The retention time was identical to the (Z,Z)-farnesol standard, indicating that the farnesyl diphosphate produced by Sh-zFPS is characterized by a Z,Z configuration type. The fact that Sh-zFPS-6His was inactive on E-geranyl diphosphate in combination with IPP indicates that this molecule is not an intermediate of Sh-zFPS-6His and produces at least one Z type bond by combining one DMAPP and one IPP. Sh-SBS was only active on the farnesyl diphosphate compound produced by Sh-zFPS, but produced at least four clearly identified sesquiterpenes, the main one being alpha-santalene. Lastly, the presence of a 6-histidine tag and spacer at the C-terminal end had no effect on enzyme activity as compared to the native enzymes of the original plant (FIG. 3).

Expression of the Z,Z-FPP synthase (Sh-zFPS) and SB synthase (Sh-SBS) genes in tobacco A trichome-specific tobacco promoter (eCBTS02, Tissier et al., 2004) was cloned upstream of the Sh-zFPS and Sh-SBS coding sequences to form the constructs eCBTS1.0-Sh-zFPS [#1] and eCBTS1.0-Sh-SBS [#2]. These two constructs were introduced into a same binary vector for transformation by *Agrobacterium*, containing a kanamycin resistance gene, yielding to the pLIBRO-064 binary vector (FIG. 2A). Construct #2 was also introduced separately into a pLIBRO-065 binary vector (FIG. 2B). The vectors were introduced into *Agrobacterium* strain LBA4404 by electroporation. Strains harboring the different vectors were used to carry out genetic transformation of *N. sylvestris* by the leaf disc method (Horsch et al., 1985).

T-DNA carrying the transgenes was introduced by genetic transformation into a *N. sylvestris* transgenic cell line (source line ihpCBTS) in which expression of the CBTS gene was inhibited by RNA interference (Tissier et al., 2005). In this line, the amount of CBT-diol in the leaves is very low. *N. sylvestris*, a wild tobacco, does not produce sesquiterpenes corresponding to those of tomato. Approximately 25 kanamycin-resistant plants were obtained for each construct. The presence of the transgenes in each plant was confirmed by PCR on leaf genomic DNA. The level of transgene expression in the leaves was checked by real time quantitative PCR on mRNA from tobacco leaves. The level of Sh-SBS transgene expression was compared to that of an actin gene constitutively expressed in tobacco leaves. The results are exemplified in FIG. 3. Results indicate that the selected lines all expressed the transgene at variable levels ranging from 1 to 50 for the pLIBRO-064 construct and from 1 to 10 for the pLIBRO-065 construct relative to the actin gene.

As olefinic sesquiterpenes are volatile molecules, the volatile molecules emitted by the plants were analyzed in a controlled atmosphere in a culture chamber. A sample of the atmosphere was captured in a derivation circuit containing a SuperQ® filter (Altech) which adsorbs olefinic terpenes. The molecules were then eluted with 1 ml pentane and analyzed by GC/MS. FIG. 7 illustrates an example of chromatographic profile of volatile molecules emitted by a transgenic plant. It shows that line #3877 expressing the Sh-zFPS and Sh-SBS genes contained several new peaks with a molecular ion signature 93, 94, 121 and 204 characteristic of this class of sesquiterpenes. The chromatographic profile was compared to that obtained on the exudate of TA517 tomato line which naturally produces these compounds (FIG. 7). The two profiles were identical and the mass spectrum of each peak was identical to that of the peaks of the TA517 line. The plants expressing the two transgenes Sh-zFPS and Sh-SBS produced alpha-santalene, epi-beta-santalene, cis-alpha-bergamotene, trans-alpha-bergamotene and endo-beta-bergamotene whereas the transgenic lines having integrated the Sh-SBS gene alone did not produce any of these compounds. These results indicate that the presence of both genes is necessary for the synthesis of sesquiterpenes of SB type. They confirm the data obtained in vitro with the recombinant enzymes. In conclusion, the Sh-zFPS and Sh-SBS genes are responsible for the biosynthesis of sesquiterpenes of tomato located at locus Sst2 described by van der Hoeven et al., 2000.

zFPS gene polymorphism between *S. lycopersicum* and *S. habrochaites*

The complete zFPS gene was amplified by PCR from genomic DNA of *S. lycopersicum*, *S. habrochaites* and TA517 using the primers ACCATGGGTTCTTTGGTTCT-TCAATGTTGGA (SEQ ID No. 9) and ACTCGAGATATGT-GTGTCCACCAAAACGTCTATG (SEQ ID No. 10). Two products were amplified in the two genomes, indicating that there are at least two copies of the gene in the two genomes (FIG. 8). One of the two products with a size of approximately 3000 nucleotides (band A) is common to the two genomes. The second product has a size of approximately 2000 nucleotides (band C) in *S. lycopersicum* and approximately 2500 nucleotides (band B) in *S. habrochaites*. The profile of the TA517 line is identical to that of *S. habrochaites*. These results indicate that gene B specific of *S. habrochaites* has been introduced in the TA517 line. Sequencing of product B confirmed that it corresponds to the zFPS gene described herein. This result also demonstrates that the zFPS gene of *S. habrochaites* can be introduced into *S. lycopersicum* by using the polymorphism which exists between the two genomes for this gene.

REFERENCES

Altschul, Stephen F., Thomas L. Madden, Alejandro A. Schäffer, Jinghui Zhang, Zheng Zhang, Webb Miller, and David J. Lipman. (1997) Gapped BLAST and PSI-BLAST: a new generation of protein database search programs. Nucleic Acids Res. 25:3389-3402.

Bates G W, Gaynor J J, Shekhawat N S. (1983) Fusion of Plant Protoplasts by Electric Fields. Plant Physiol. 72:1110-1113.

Bohlmann J, Crock J, Jetter R, Croteau R. (1998) Terpenoid-based defenses in conifers: cDNA cloning, characterization, and functional expression of wound-inducible (E)-alpha-bisabolene synthase from grand fir (Abies grandis). Proc. Natl. Acad. Sci. USA. 95:6756-6761.

Bouwmeester H J, Kodde J, Verstappen F W, Altug I G, de Kraker J W, Wallaart T E. (2002) Isolation and characterization of two germacrene A synthase cDNA clones from chicory. Plant Physiol. 29:134-144.

Cai Y, Jia J W, Crock J, Lin Z X, Chen X Y, Croteau R. (2002) A cDNA clone for beta-caryophyllene synthase from *Artemisia annua*. Phytochemistry 61:523-529.

Cane D E. (1999) Sesquiterpene biosynthesis: Cyclization mechanisms. In comprehensive natural products chemistry, isoprenoids including carotenoids and steroids, Vol. 2, D. D. Cane, ed (Amsterdam, The Netherlands; Elsever), pp. 155-200.

Carman R M, Duffield A R (1993) The Biosynthesis of Labdanoids—the Optical Purity of Naturally-Occurring Manool and Abienol. Aust. J. Chem. 46:1105-1114.

Clarke C F, Tanaka R D, Svenson K, Wamsley M, Fogelman A M, Edwards P A. (1987) Molecular cloning and sequence of a cholesterol-repressible enzyme related to prenyltransferase in the isoprene biosynthetic pathway. Mol. Cell. Biol. 7:3138-3146.

Colby S M, Crock J, Dowdle-Rizzo B, Lemaux P G, Croteau R. (1998) Germacrene C synthase from *Lycopersicon esculentum* cv. VFNT cherry tomato: cDNA isolation, characterization, and bacterial expression of the multiple product sesquiterpene cyclase. Proc. Natl. Acad. Sci. USA 95:2216-2221.

Facchini P J, Chappell J. (1992) Gene family for an elicitor-induced sesquiterpene cyclase in tobacco. Proc. Natl. Acad. Sci. USA 89(22):11088-11092.

Heinstein P F, Herman D L, Tove S B, Smith F H. (1970) Biosynthesis of gossypol. Incorporation of mevalonate-2-$^{14}$C and isoprenyl pyrophosphates J. Biol. Chem. 245: 4658-4665.

Horsch R B, Rogers S G, Fraley R T. (1985) Transgenic plants. Cold Spring Harb Symp Quant Biol. 50:433-437.

Kharel Y, Takahashi S, Yamashita S, Koyama T. (2006) Manipulation of prenyl chain length determination mechanism of cis-prenyltransferases. FEBS J. 273:647-657.

Kollner T G, O'Maille P E, Gatto N, Boland W, Gershenzon J, Degenhardt J. (2006) Two pockets in the active site of maize sesquiterpene synthase TPS4 carry out sequential parts of the reaction scheme resulting in multiple products. Arch. Biochem. Biophys. 448:83-92.

Koyama T. (1999) Molecular analysis of prenyl chain elongation enzymes. Biosci. Biotechnol. Biochem. 63:1671-1676.

Liang P H, Ko T P, Wang A R (2002) Structure, mechanism and function of prenyltransferases. 269:3339-3354.

Marchler-Bauer A, Bryant S H. (2004) CD-Search: protein domain annotations on the fly. Nucleic Acids Res. 32(W): 327-331.

McMillan J., and Beale M. H. (1999) Dipterpene biosynthesis. In comprehensive natural products chemistry, isoprenoids including carotenoids and steroids Vol. 2, D. D. Cane, ed (Amsterdam, The Netherlands; Elsever), pp. 217-243.

Monforte A J, Tanksley S D. (2000) Development of a set of near isogenic and backcross recombinant inbred lines containing most of the *Lycopersicon hirsutum* genome in an *L. esculentum* background: A tool for gene mapping and gene discovery. Genomics 43:803-813.

Oh S K, Han K H, Ryu S B, Kang H. (2000) Molecular cloning, expression, and functional analysis of a cis-prenyltransferase from *Arabidopsis thaliana*. Implications in rubber biosynthesis. J. Biol. Chem. 275:18482-18488.

Poulter D C. (2006) Farnesyl Diphosphate Synthase. A Paradigm for Understanding Structure and Function Relationships in E-polyprenyl Diphosphate Synthases. Phytochem. Review 5:17-26.

Rodriguez-Concepcion M, Boronat A. (2002) Elucidation of the methylerythritol phosphate pathway for isoprenoid biosynthesis in bacteria and plastids. A metabolic milestone achieved through genomics. Plant Physiol. 130(3):1079-89.

Sharon-Asa L, Shalit M, Frydman A, Bar E, Holland D, Or E, Lavi U, Lewinsohn E, Eyal Y. (2003) Citrus fruit flavor and aroma biosynthesis: isolation, functional characterization, and developmental regulation of Cstps1, a key gene in the production of the sesquiterpene aroma compound valencene. Plant J. 36:664-74.

Shimizu N, Koyama T, Ogura K. (1998) Molecular cloning, expression, and purification of undecaprenyl diphosphate synthase. No sequence similarity between E- and Z-prenyl diphosphate synthases. J. Biol. Chem. 273:19476-19481.

Schulbach M C, Brennan P J, Crick D C. (2000) Identification of a short (C15) chain Z-isoprenyl diphosphate synthase and a homologous long (C50) chain isoprenyl diphosphate synthase in *Mycobacterium tuberculosis*. J. Biol. Chem. 275:22876-22881.

Tarshis L C, Yan M, Poulter C D, Sacchettini J C. (1994) Crystal structure of recombinant farnesyl diphosphate synthase at 2.6-A resolution. Biochemistry 33:10871-10877.

Tholl D. (2006) Terpene synthases and the regulation, diversity and biological roles of terpene metabolism. Curr. Opin. Plant Biol. 9:297-304.

Thompson, J D, Gibson, T J, Plewniak, F, Jeanmougin, F, and Higgins, D G. (1997) The ClustalX windows interface: flexible strategies for multiple sequence alignment aided by quality analysis tools. Nucleic Acids Res. 24:4876-4882.

Tissier A, Sallaud C, Rontein D. (2004) Promoteurs vegetaux et utilisation PCT/FR 05/02530.

Tissier A, Sallaud C, Rontein D. (2005) Systeme de production de terpenes dans les plantes. French patent application FR 05 00855.

van Der Hoeven R S, Monforte A J, Breeden D, Tanksley S D, Steffens J C. (2000) Free in PMC Genetic control and evolution of sesquiterpene biosynthesis in *Lycopersicon esculentum* and *L. hirsutum*. Plant Cell. 12:2283-2294.

Wallaart T E, Bouwmeester H J, Hille J, Popping a L, Maijers N C. (2001) Amorpha-4,11-diene synthase: cloning and functional expression of a key enzyme in the biosynthetic pathway of the novel antimalarial drug artemisinin. Planta. 212:460-465.

Wang K, Ohnuma Sl. (1999) Chain-length determination mechanism of isoprenyl diphosphate synthases and implications for molecular evolution. 24:445-451.

Wise M L, Croteau R A. (1999) Monoterpene biosynthesis. In comprehensive natural products chemistry, isoprenoids including carotenoids and steroids Vol. 2, D. D. Cane, ed (Amsterdam, The Netherlands; Elsever), pp. 97-153.

Zimmermann U, Scheurich P. (1981) High frequency fusion of plant protoplasts by electric fields. Planta 151:26-32.

The invention claimed is:

1. A method for producing sesquiterpenes in a cell comprising:
   a) introducing into said cell a construct having an expression cassette comprising a first gene encoding a Z,Z-farnesyl diphosphate synthase (zFPS) comprising SEQ ID NO: 2 and a construct having an expression cassette comprising a second gene encoding a SB synthase (SBS) comprising SEQ ID NO: 4; and
   b) growing the transformed cell in the presence of isopentenyl diphosphate (IPP) and dimethylallyl diphosphate (DMAPP) under conditions suitable for the expression of said first and said second genes.

2. The method according to claim 1, further comprising collecting said sesquiterpenes contained in said cell and/or in culture medium containing said cell.

3. A cDNA encoding a protein comprising SEQ ID NO: 2 or SEQ ID NO: 4.

4. A vector comprising a nucleic acid encoding a protein comprising SEQ ID NO: 2 or SEQ ID NO: 4.

5. The vector according to claim 4 comprising an expression cassette, said expression cassette comprising the nucleic acid encoding a protein comprising SEQ ID NO: 2 or SEQ ID NO: 4.

6. An isolated bacterial or plant host cell transformed with a nucleic acid encoding a protein comprising SEQ ID NO: 2 or SEQ ID NO: 4.

7. A transgenic plant comprising a heterologous nucleic acid, said heterologous nucleic acid comprising a nucleic acid encoding a protein comprising SEQ ID NO: 2 or SEQ ID NO: 4.

8. The transgenic plant according to claim 7, wherein the plant comprises a glandular trichome.

9. The transgenic plant according to claim 8, wherein the plant belongs to the genera of *Nicotiana* or *Solanum* plants.

10. The transgenic plant according to claim 7, wherein the transgenic plant is selected from the following genera: *Asteraceae, Cannabaceae, Solanaceae, Lamiaceae, Populus, Nicotiana, Cannabis, Pharbitis, Apteria, Psychotria, Mercurialis, Chrysanthemum, Polypodium, Pelargonium, Mimulus, Matricaria, Monarda, Solanum, Achillea, Valeriana, Ocimum, Medicago, Aesculus, Plumbago, Pityrogramma, Phacelia, Avicennia, Tamarix, Frankenia, Limonium, Foeniculum, Thymus, Salvia, Kadsura, Beyeria, Humulus, Mentha, Artemisia, Nepta, Geraea, Pogostemon, Majorana, Cleome, Cnicus, Parthenium, Ricinocarpos, Hymennaea, Larrea, Primula, Phacelia, Dryopteris, Plectranthus, Cypripedium, Petunia, Datura, Mucuna, Ricinus, Hypericum, Myoporum, Acacia, Diplopeltis, Dodonaea, Halgania, Cyanostegia, Prostanthera, Anthocercis, Olearia,* or *Viscaria.*

11. The transgenic plant according to claim 7, wherein the transgenic plant is selected from the group consisting of sunflower, tomato, tobacco, potato, pepper, eggplant, mint, basil, lavender and thyme.

12. The transgenic plant according to claim 7, wherein the transgenic plant is selected from *Nicotiana tabacum, Nicotiana sylvestris, Solanum lycopersicum* or *Solanum habrochaites.*

13. A method for producing Z,Z-farnesyl diphosphate (Z,Z-FPP) comprising:
   a) providing plant cells or bacterial cells comprising an expression cassette, said expression cassette comprising a nucleic acid sequence encoding a protein comprising SEQ ID NO: 2 having Z,Z-FPP synthase activity; and
   b) growing the plant cells or bacterial cells in the presence of isopentenyl diphosphate and dimethylallyl diphosphate and under conditions suitable for the expression of the protein.

14. A method for producing sesquiterpenes comprising:
   a) providing plant cells or bacterial cells comprising a first an expression cassette comprising a first nucleic acid sequence encoding a first protein comprising SEQ ID NO: 2, and a second expression cassette comprising a second nucleic acid sequence encoding a second protein comprising SEQ ID NO: 4; and
   b) growing the plant cells or bacterial cells in the presence of isopentenyl diphosphate and dimethylallyl diphosphate and under conditions suitable for the expression of the first protein and the second protein.

15. A method for producing sesquiterpenes comprising:
   a) providing plant cells or bacterial cells comprising an expression cassette, said expression cassette comprising a nucleic acid sequence encoding a protein comprising SEQ ID NO: 4; and
   b) growing the plant cells or bacterial cells in the presence of Z,Z-farnesyl diphosphate and under conditions suitable for the expression of the protein.

16. A method for producing sesquiterpenes in a multicellular plant wherein the multicellular plant does not produce the sesquiterpenes or the amount of the sesquiterpenes produced in the multicellular plant is to be increased, said method comprising providing a transgenic multicellular plant that is prepared by a process comprising:
　a) introducing into plant cells a construct comprising an expression cassette, said expression cassette comprising a nucleic acid sequence encoding a protein comprising SEQ ID NO: 2, a nucleic acid sequence encoding a protein comprising SEQ ID NO: 4 or both a nucleic acid sequence encoding a protein comprising SEQ ID NO: 2 and a nucleic acid sequence encoding a protein comprising SEQ ID NO: 4; and,
　b) reconstituting multicellular plants from said plant cells and selecting the transgenic multicellular plants that are expressing the introduced nucleic acid sequence.

17. The method according to claim 16, wherein in step a), an expression cassette comprising a nucleic acid sequence encoding SEQ ID NO: 2 and a nucleic acid sequence encoding SEQ ID NO: 4 are introduced into the plant cells and in step b), a transgenic multicellular plant expressing both of the introduced nucleic acid sequences are selected.

18. A plant seed comprising an expression cassette, said expression cassette comprising a nucleic acid sequence encoding a protein comprising SEQ ID NO: 2, SEQ ID NO: 4 or both SEQ ID NO: 2 and SEQ ID NO: 4.

19. The method according to claim 13, wherein the plant cells that are grown in step b) are part of a multicellular plant.

20. The method according to claim 14, wherein the plant cells that are grown in step b) are part of a multicellular plant.

21. The method according to claim 15, wherein the plant cells that are grown in step b) are part of a multicellular plant.

22. The method according to claim 13, further comprising introducing into a plant cell a construct having an expression cassette with a nucleic acid sequence encoding a protein comprising SEQ ID NO: 2 in step (a).

23. The method according to claim 15, further comprising introducing into a plant cell a construct having an expression cassette with a nucleic acid sequence encoding a protein comprising SEQ ID NO: 4 in step (a).

24. The method according to claim 16, said expression cassette comprises a nucleic acid sequence encoding a protein comprising SEQ ID NO: 2.

\* \* \* \* \*

UNITED STATES PATENT AND TRADEMARK OFFICE
CERTIFICATE OF CORRECTION

PATENT NO.         : 8,629,321 B2
APPLICATION NO.    : 12/593688
DATED              : January 14, 2014
INVENTOR(S)        : Christophe Sallaud, Denis Rontein and Alain Tissier It is certified that error appears in the above-identified patent and that said Letters Patent is hereby corrected as shown below:

In the Specification

Column 3,
Line 9, "rectional" should read --reactional--.

Column 7,
Line 32, "ZZ-FPS" should read --Z,Z-FPS--.
Line 39, "4Z-farnesyl" should read --Z,Z-farnesyl--.

Column 8,
Line 64, "cis-alpha -bergamotene,trans-alpha-bergamotene" should read
    --*cis*-alpha-bergamotene, *trans*-alpha-bergamotene--.

Column 9,
Line 47, "IPPP," should read --IPP,--.

Column 10,
Line 8, "IPPP," should read --IPP,--.

Column 12,
Lines 10-25,
    "from IPP and DMAPP.
        The present invention relates to a method for producing Z,Z-FPP or derivatives
    thereof from IPP and DMAP comprising contacting IPP and DMAP with a purified
    or recombinant Z,Z-FPP synthase with at least 80%, 85%, 90%, 95%, 97%, 98% or
    99% identity to SEQ ID No. 2 in suitable conditions and collecting the obtained
    Z,Z-FPP or derivatives thereof. Optionally, the method further comprises incubating
    Z,Z-FPP obtained with a calf intestine alkaline phosphatase and collecting Z,Z-farnsol.
    The present invention relates to the use of a purified or recombinant Z,Z-FPP Signed and Sealed this
Fourteenth Day of April, 2015

Michelle K. Lee
*Director of the United States Patent and Trademark Office* synthase with at least 80%, 85%, 90%, 95%, 97%, 98% or 99% identity to SEQ ID No. 2 for preparing Z,Z-FPP or derivatives thereof from IPP and DMAP.
    The present invention relates to a method for producing a mixture of class II" should read
    --from IPP and DMAPP.
    The present invention relates to a method for producing a mixture of class II--.
Line 29, "a obtained" should read --an obtained--.
Line 62, "staining, a light emission" should read --staining, or a light emission--.

Column 13,
Lines 6-8, "pQE-30
    (QIAGEN)." should read --pQE-30 (QIAGEN).--.
Line 52, "IPPP" should read --IPP--.

Column 15,
Line 36, "Cannabaceae *Cannabis sativa*)" should read
    --*Cannabaceae* (e.g., *Cannabis sativa*)--.

Column 16,
Line 15, "1852 by" should read --1852 bp--.

Column 18,
Line 50, "synthase Inhibition" should read --synthase. Inhibition--.

Column 19,
Lines 57-58, "*S. habrochaites*tomato leaf" should read --*S. habrochaites* tomato leaf--.

Column 25,
Line 35, "Wang A R" should read --Wang A H--.

Column 26,
Line 33, "et utilisation" should read --et utilisations--.
Line 47, "Ohnuma S1." should read --Ohnuma SI.--.

SEQUENCE LISTING

<160> NUMBER OF SEQ ID NOS: 10

<210> SEQ ID NO 1
<211> LENGTH: 912
<212> TYPE: DNA

<213> ORGANISM: Solanum abutiloides
<220> FEATURE:
<221> NAME/KEY: CDS
<222> LOCATION: (1)..(912)

<400> SEQUENCE: 1

```
atg agt tct ttg gtt ctt caa tgt tgg aaa tta tca tct cca tct ctg      48
Met Ser Ser Leu Val Leu Gln Cys Trp Lys Leu Ser Ser Pro Ser Leu
 1               5                  10                  15 att tta caa caa aat aca tca ata tcc atg ggt gca ttc aaa ggt att      96
Ile Leu Gln Gln Asn Thr Ser Ile Ser Met Gly Ala Phe Lys Gly Ile
            20                  25                  30 cat aaa ctt caa atc cca aat tca cct ctg aca gtg tct gct cgt gga    144
His Lys Leu Gln Ile Pro Asn Ser Pro Leu Thr Val Ser Ala Arg Gly
        35                  40                  45 ctc aac aag att tca tgc tca ctc agc tta caa acc gaa aaa ctt tgt    192
Leu Asn Lys Ile Ser Cys Ser Leu Ser Leu Gln Thr Glu Lys Leu Cys
50                  55                  60 tat gag gat aat gat aat gat ctt gat gaa gaa ctt atg cct aaa cac    240
Tyr Glu Asp Asn Asp Asn Asp Leu Asp Glu Glu Leu Met Pro Lys His
65                  70                  75                  80 att gct ttg ata atg gat ggt aat agg aga tgg gca aag gat aag ggt    288
Ile Ala Leu Ile Met Asp Gly Asn Arg Arg Trp Ala Lys Asp Lys Gly
                85                  90                  95 tta gac gta tcc gaa ggt cac aaa cat ctc ttt cca aaa tta aaa gag    336
Leu Asp Val Ser Glu Gly His Lys His Leu Phe Pro Lys Leu Lys Glu
            100                 105                 110 att tgt gac att tct tct aaa ttg gga ata caa gtt atc act gct ttt    384
Ile Cys Asp Ile Ser Ser Lys Leu Gly Ile Gln Val Ile Thr Ala Phe
        115                 120                 125 gca ttc tct act gaa aat tgg aaa cga gcc aag ggg gag gtt gat ttc    432
Ala Phe Ser Thr Glu Asn Trp Lys Arg Ala Lys Gly Glu Val Asp Phe
    130                 135                 140 ttg atg caa atg ttc gaa gaa ctc tat gat gag ttt tcg agg tct gga    480
Leu Met Gln Met Phe Glu Glu Leu Tyr Asp Glu Phe Ser Arg Ser Gly
145                 150                 155                 160 gta aga gtg tct att att ggt tgt aaa acc gac ctc cca atg aca tta    528
Val Arg Val Ser Ile Ile Gly Cys Lys Thr Asp Leu Pro Met Thr Leu
                165                 170                 175 caa aaa tgc ata gca tta aca gaa gag act aca aag gga aac aaa gga    576
Gln Lys Cys Ile Ala Leu Thr Glu Glu Thr Thr Lys Gly Asn Lys Gly
            180                 185                 190 ctt cac ctt gtg att gca cta aac tat ggt ggc tat tat gac ata ttg    624
Leu His Leu Val Ile Ala Leu Asn Tyr Gly Gly Tyr Tyr Asp Ile Leu
        195                 200                 205 caa gca aca aaa agc att gtt aat aaa gca atg aat ggt tta tta gat    672
Gln Ala Thr Lys Ser Ile Val Asn Lys Ala Met Asn Gly Leu Leu Asp
    210                 215                 220 gta gaa gat atc aac aag aat tta ttt gat caa gaa ctt gaa agc aag    720
Val Glu Asp Ile Asn Lys Asn Leu Phe Asp Gln Glu Leu Glu Ser Lys
225                 230                 235                 240 tgt cca aat cct gat tta ctt ata agg aca gga ggt gat caa aga gtt    768
Cys Pro Asn Pro Asp Leu Leu Ile Arg Thr Gly Gly Asp Gln Arg Val
                245                 250                 255 agt aac ttt ttg ttg tgg caa ttg gct tat act gaa ttt tac ttc acc    816
Ser Asn Phe Leu Leu Trp Gln Leu Ala Tyr Thr Glu Phe Tyr Phe Thr
            260                 265                 270 aaa aca ttg ttt cct gat ttt gga gag gaa gat ctt aaa gag gca ata    864
Lys Thr Leu Phe Pro Asp Phe Gly Glu Glu Asp Leu Lys Glu Ala Ile
        275                 280                 285 ata aac ttt caa caa agg cat aga cgt ttt ggt gga cac aca tat tga    912
Ile Asn Phe Gln Gln Arg His Arg Arg Phe Gly Gly His Thr Tyr
    290                 295                 300
```

```
Ile Asn Phe Gln Gln Arg His Arg Arg Phe Gly Gly His Thr Tyr
    290                 295                 300
```

```
<210> SEQ ID NO 2
<211> LENGTH: 303
<212> TYPE: PRT
<213> ORGANISM: Solanum abutiloides

<400> SEQUENCE: 2
```

```
Met Ser Ser Leu Val Leu Gln Cys Trp Lys Leu Ser Pro Ser Leu
1               5                   10                  15

Ile Leu Gln Gln Asn Thr Ser Ile Ser Met Gly Ala Phe Lys Gly Ile
            20                  25                  30

His Lys Leu Gln Ile Pro Asn Ser Pro Leu Thr Val Ser Ala Arg Gly
            35                  40                  45

Leu Asn Lys Ile Ser Cys Ser Leu Ser Leu Gln Thr Glu Lys Leu Cys
    50                  55                  60

Tyr Glu Asp Asn Asp Asn Asp Leu Asp Glu Leu Met Pro Lys His
65                  70                  75                  80

Ile Ala Leu Ile Met Asp Gly Asn Arg Arg Trp Ala Lys Asp Lys Gly
                85                  90                  95

Leu Asp Val Ser Glu Gly His Lys His Leu Phe Pro Lys Leu Lys Glu
            100                 105                 110

Ile Cys Asp Ile Ser Ser Lys Leu Gly Ile Gln Val Ile Thr Ala Phe
            115                 120                 125

Ala Phe Ser Thr Glu Asn Trp Lys Arg Ala Lys Gly Glu Val Asp Phe
    130                 135                 140

Leu Met Gln Met Phe Glu Glu Leu Tyr Asp Glu Phe Ser Arg Ser Gly
145                 150                 155                 160

Val Arg Val Ser Ile Ile Gly Cys Lys Thr Asp Leu Pro Met Thr Leu
                165                 170                 175

Gln Lys Cys Ile Ala Leu Thr Glu Glu Thr Thr Lys Gly Asn Lys Gly
            180                 185                 190

Leu His Leu Val Ile Ala Leu Asn Tyr Gly Gly Tyr Tyr Asp Ile Leu
        195                 200                 205

Gln Ala Thr Lys Ser Ile Val Asn Lys Ala Met Asn Gly Leu Leu Asp
    210                 215                 220

Val Glu Asp Ile Asn Lys Asn Leu Phe Asp Gln Glu Leu Glu Ser Lys
225                 230                 235                 240

Cys Pro Asn Pro Asp Leu Leu Ile Arg Thr Gly Gly Asp Gln Arg Val
                245                 250                 255

Ser Asn Phe Leu Leu Trp Gln Leu Ala Tyr Thr Glu Phe Tyr Phe Thr
            260                 265                 270

Lys Thr Leu Phe Pro Asp Phe Gly Glu Glu Asp Leu Lys Glu Ala Ile
        275                 280                 285

Ile Asn Phe Gln Gln Arg His Arg Arg Phe Gly Gly His Thr Tyr
    290                 295                 300
```

```
<210> SEQ ID NO 3
<211> LENGTH: 2334
<212> TYPE: DNA
<213> ORGANISM: Solanum habrochaites
<220> FEATURE:
<221> NAME/KEY: CDS
<222> LOCATION: (1)..(2334)

<400> SEQUENCE: 3
```

```
atg ata gtt ggc tat aga agc aca atc ata acc ctt tct cat cct aag        48
```

```
            Met Ile Val Gly Tyr Arg Ser Thr Ile Ile Thr Leu Ser His Pro Lys
            1               5                   10                  15 cta ggc aat ggg aaa aca att tca tcc aat gca att ttc cag aga tca        96
Leu Gly Asn Gly Lys Thr Ile Ser Ser Asn Ala Ile Phe Gln Arg Ser
            20                  25                  30 tgt aga gta aga tgc agc cac agt acc cct tca tca atg aat ggt ttc       144
Cys Arg Val Arg Cys Ser His Ser Thr Pro Ser Ser Met Asn Gly Phe
            35                  40                  45 gaa gat gca agg gat aga ata agg gaa agt ttt ggg aaa gta gag tta       192
Glu Asp Ala Arg Asp Arg Ile Arg Glu Ser Phe Gly Lys Val Glu Leu
50                  55                  60 tct cct tct tcc tat gac aca gca tgg gta gct atg gtc cct tca aaa       240
Ser Pro Ser Ser Tyr Asp Thr Ala Trp Val Ala Met Val Pro Ser Lys
65                  70                  75                  80 cat tca cta aat gag cca tgt ttt cca caa tgt ttg gat tgg att att       288
His Ser Leu Asn Glu Pro Cys Phe Pro Gln Cys Leu Asp Trp Ile Ile
            85                  90                  95 gaa aat caa aga gaa gat gga tct tgg gga cta aac cct agc cat cca       336
Glu Asn Gln Arg Glu Asp Gly Ser Trp Gly Leu Asn Pro Ser His Pro
            100                 105                 110 ttg ctt ctc aag gac tca ctt tct tcc act ctt gca tgt ttg ctt gca       384
Leu Leu Leu Lys Asp Ser Leu Ser Ser Thr Leu Ala Cys Leu Leu Ala
            115                 120                 125 cta acc aaa tgg aga gtt gga gat gag caa atc aaa aga ggc ctt ggc       432
Leu Thr Lys Trp Arg Val Gly Asp Glu Gln Ile Lys Arg Gly Leu Gly
130                 135                 140 ttt att gaa acc cag agt tgg gca att gat aac aag gat caa att tca       480
Phe Ile Glu Thr Gln Ser Trp Ala Ile Asp Asn Lys Asp Gln Ile Ser
145                 150                 155                 160 cct cta gga ttt gaa att ata ttt ccc agt atg atc aag tct gca gaa       528
Pro Leu Gly Phe Glu Ile Ile Phe Pro Ser Met Ile Lys Ser Ala Glu
            165                 170                 175 aaa cta aac tta aat cta gca att aac aaa aga gat tca aca att aaa       576
Lys Leu Asn Leu Asn Leu Ala Ile Asn Lys Arg Asp Ser Thr Ile Lys
            180                 185                 190 aga gca tta cag aat gag ttc acg agg aat att gaa tat atg agt gaa       624
Arg Ala Leu Gln Asn Glu Phe Thr Arg Asn Ile Glu Tyr Met Ser Glu
            195                 200                 205 gga gtt ggt gaa tta tgt gat tgg aag gaa ata ata aag tta cat caa       672
Gly Val Gly Glu Leu Cys Asp Trp Lys Glu Ile Ile Lys Leu His Gln
210                 215                 220 agg caa aat ggt tca tta ttt gat tca cca gcc act act gca gct gcc       720
Arg Gln Asn Gly Ser Leu Phe Asp Ser Pro Ala Thr Thr Ala Ala Ala
225                 230                 235                 240 ttg att tac cat cag cat gat aaa aaa tgc tat gaa tat ctt aat tca       768
Leu Ile Tyr His Gln His Asp Lys Lys Cys Tyr Glu Tyr Leu Asn Ser
            245                 250                 255 atc ttg caa caa cac aaa aat tgg gtt ccc act atg tat cca aca aag       816
Ile Leu Gln Gln His Lys Asn Trp Val Pro Thr Met Tyr Pro Thr Lys
            260                 265                 270 ata cat tca ttg ctt tgc ttg gtt gat aca ctt caa aat ctt gga gta       864
Ile His Ser Leu Leu Cys Leu Val Asp Thr Leu Gln Asn Leu Gly Val
            275                 280                 285 cat cgg cat ttt aaa tca gaa ata aag aaa gct cta gat gaa ata tac       912
His Arg His Phe Lys Ser Glu Ile Lys Lys Ala Leu Asp Glu Ile Tyr
            290                 295                 300 agg cta tgg caa caa aag aat gaa caa att ttc tca aat gtc acc cat       960
Arg Leu Trp Gln Gln Lys Asn Glu Gln Ile Phe Ser Asn Val Thr His
305                 310                 315                 320 tgt gct atg gct ttt cga ctt cta agg atg agc tac tat gat gtc tcc      1008
```

-continued

| | | | | | | | | | | | | | | | |
|---|---|---|---|---|---|---|---|---|---|---|---|---|---|---|---|
| Cys | Ala | Met | Ala | Phe | Arg | Leu | Leu | Arg | Met | Ser | Tyr | Tyr | Asp | Val | Ser |
| | | | 325 | | | | | 330 | | | | | 335 | | |

| tca | gat | gaa | cta | gca | gaa | ttt | gtg | gat | gaa | gaa | cat | ttt | ttt | gca | ata | 1056 |
|---|---|---|---|---|---|---|---|---|---|---|---|---|---|---|---|---|
| Ser | Asp | Glu | Leu | Ala | Glu | Phe | Val | Asp | Glu | Glu | His | Phe | Phe | Ala | Ile | |
| | | | 340 | | | | | 345 | | | | | 350 | | | |

| agt | ggg | aaa | tat | aca | agt | cat | gtt | gaa | att | ctt | gaa | ctc | cac | aaa | gca | 1104 |
|---|---|---|---|---|---|---|---|---|---|---|---|---|---|---|---|---|
| Ser | Gly | Lys | Tyr | Thr | Ser | His | Val | Glu | Ile | Leu | Glu | Leu | His | Lys | Ala | |
| | | | 355 | | | | | 360 | | | | | 365 | | | |

| tca | caa | ttg | gct | att | gat | cat | gag | aaa | gat | gac | att | ttg | gat | aag | att | 1152 |
|---|---|---|---|---|---|---|---|---|---|---|---|---|---|---|---|---|
| Ser | Gln | Leu | Ala | Ile | Asp | His | Glu | Lys | Asp | Asp | Ile | Leu | Asp | Lys | Ile | |
| | 370 | | | | | 375 | | | | | 380 | | | | | |

| aac | aat | tgg | aca | aga | aca | ttt | atg | gag | caa | aaa | ctc | tta | aac | aat | ggc | 1200 |
|---|---|---|---|---|---|---|---|---|---|---|---|---|---|---|---|---|
| Asn | Asn | Trp | Thr | Arg | Thr | Phe | Met | Glu | Gln | Lys | Leu | Leu | Asn | Asn | Gly | |
| 385 | | | | | 390 | | | | | 395 | | | | | 400 | |

| ttc | ata | gat | agg | atg | tca | aaa | aag | gag | gtg | gaa | ctt | gct | ttg | agg | aag | 1248 |
|---|---|---|---|---|---|---|---|---|---|---|---|---|---|---|---|---|
| Phe | Ile | Asp | Arg | Met | Ser | Lys | Lys | Glu | Val | Glu | Leu | Ala | Leu | Arg | Lys | |
| | | | | 405 | | | | | 410 | | | | | 415 | | |

| ttt | tat | acc | ata | tct | gat | cta | gca | gaa | aat | aga | aga | tgt | ata | aag | tca | 1296 |
|---|---|---|---|---|---|---|---|---|---|---|---|---|---|---|---|---|
| Phe | Tyr | Thr | Ile | Ser | Asp | Leu | Ala | Glu | Asn | Arg | Arg | Cys | Ile | Lys | Ser | |
| | | | 420 | | | | | 425 | | | | | 430 | | | |

| tac | gaa | gag | aac | aat | ttt | aaa | atc | tta | aaa | gca | gct | tat | agg | tca | cct | 1344 |
|---|---|---|---|---|---|---|---|---|---|---|---|---|---|---|---|---|
| Tyr | Glu | Glu | Asn | Asn | Phe | Lys | Ile | Leu | Lys | Ala | Ala | Tyr | Arg | Ser | Pro | |
| | | | | 435 | | | | | 440 | | | | | 445 | | |

| aac | att | tac | aat | aag | gac | ttg | ttt | ata | ttt | tca | ata | cgc | aac | ttt | gaa | 1392 |
|---|---|---|---|---|---|---|---|---|---|---|---|---|---|---|---|---|
| Asn | Ile | Tyr | Asn | Lys | Asp | Leu | Phe | Ile | Phe | Ser | Ile | Arg | Asn | Phe | Glu | |
| | 450 | | | | | 455 | | | | | 460 | | | | | |

| tta | tgc | caa | gct | caa | cac | caa | gaa | gaa | ctt | caa | caa | ttc | aag | agg | tgg | 1440 |
|---|---|---|---|---|---|---|---|---|---|---|---|---|---|---|---|---|
| Leu | Cys | Gln | Ala | Gln | His | Gln | Glu | Glu | Leu | Gln | Gln | Phe | Lys | Arg | Trp | |
| 465 | | | | | 470 | | | | | 475 | | | | | 480 | |

| ttt | gaa | gat | tat | aga | ttg | gac | caa | ctc | gga | att | gca | gaa | cga | tat | ata | 1488 |
|---|---|---|---|---|---|---|---|---|---|---|---|---|---|---|---|---|
| Phe | Glu | Asp | Tyr | Arg | Leu | Asp | Gln | Leu | Gly | Ile | Ala | Glu | Arg | Tyr | Ile | |
| | | | | 485 | | | | | 490 | | | | | 495 | | |

| cat | gat | act | tac | tta | tgt | gct | gtt | att | gtt | gtc | ccc | gag | cct | gaa | tta | 1536 |
|---|---|---|---|---|---|---|---|---|---|---|---|---|---|---|---|---|
| His | Asp | Thr | Tyr | Leu | Cys | Ala | Val | Ile | Val | Val | Pro | Glu | Pro | Glu | Leu | |
| | | | 500 | | | | | 505 | | | | | 510 | | | |

| tcc | gat | gct | cgt | ctc | ttg | tac | gcg | aaa | tac | gtc | ttg | ctc | ctg | act | att | 1584 |
|---|---|---|---|---|---|---|---|---|---|---|---|---|---|---|---|---|
| Ser | Asp | Ala | Arg | Leu | Leu | Tyr | Ala | Lys | Tyr | Val | Leu | Leu | Leu | Thr | Ile | |
| | | | 515 | | | | | 520 | | | | | 525 | | | |

| gtc | gat | gat | cag | ttc | gac | agt | ttt | gca | tct | aca | gat | gaa | tgt | ctc | aac | 1632 |
|---|---|---|---|---|---|---|---|---|---|---|---|---|---|---|---|---|
| Val | Asp | Asp | Gln | Phe | Asp | Ser | Phe | Ala | Ser | Thr | Asp | Glu | Cys | Leu | Asn | |
| | 530 | | | | | 535 | | | | | 540 | | | | | |

| atc | att | gaa | tta | gta | gaa | agg | tgg | gat | gac | tat | gca | agt | gta | ggt | tat | 1680 |
|---|---|---|---|---|---|---|---|---|---|---|---|---|---|---|---|---|
| Ile | Ile | Glu | Leu | Val | Glu | Arg | Trp | Asp | Asp | Tyr | Ala | Ser | Val | Gly | Tyr | |
| 545 | | | | | 550 | | | | | 555 | | | | | 560 | |

| aaa | tct | gag | aag | gtt | aaa | gtt | ttc | ttt | tca | act | ttg | tac | aaa | tca | ata | 1728 |
|---|---|---|---|---|---|---|---|---|---|---|---|---|---|---|---|---|
| Lys | Ser | Glu | Lys | Val | Lys | Val | Phe | Phe | Ser | Thr | Leu | Tyr | Lys | Ser | Ile | |
| | | | | 565 | | | | | 570 | | | | | 575 | | |

| gag | gag | ctt | gta | aca | att | gct | gaa | att | aaa | caa | gga | cga | tct | gtc | aaa | 1776 |
|---|---|---|---|---|---|---|---|---|---|---|---|---|---|---|---|---|
| Glu | Glu | Leu | Val | Thr | Ile | Ala | Glu | Ile | Lys | Gln | Gly | Arg | Ser | Val | Lys | |
| | | | 580 | | | | | 585 | | | | | 590 | | | |

| aat | cac | ctt | ctt | aat | ttg | tgg | ctt | gaa | ttg | gtg | aag | ttg | atg | ttg | atg | 1824 |
|---|---|---|---|---|---|---|---|---|---|---|---|---|---|---|---|---|
| Asn | His | Leu | Leu | Asn | Leu | Trp | Leu | Glu | Leu | Val | Lys | Leu | Met | Leu | Met | |
| | | 595 | | | | | 600 | | | | | 605 | | | | |

| gaa | cga | gta | gag | tgg | ttt | tct | ggc | aag | aca | atc | cca | agc | ata | gaa | gag | 1872 |
|---|---|---|---|---|---|---|---|---|---|---|---|---|---|---|---|---|
| Glu | Arg | Val | Glu | Trp | Phe | Ser | Gly | Lys | Thr | Ile | Pro | Ser | Ile | Glu | Glu | |
| | | 610 | | | | | 615 | | | | | 620 | | | | |

| tat | ttg | tat | gtt | aca | tct | ata | aca | ttt | ggt | gca | aga | ttg | att | cct | ctc | 1920 |
|---|---|---|---|---|---|---|---|---|---|---|---|---|---|---|---|---|
| Tyr | Leu | Tyr | Val | Thr | Ser | Ile | Thr | Phe | Gly | Ala | Arg | Leu | Ile | Pro | Leu | |
| 625 | | | | | 630 | | | | | 635 | | | | | 640 | |

| aca | aca | caa | tat | ttt | ctt | gga | ata | aaa | ata | tcc | gaa | gat | att | tta | gaa | 1968 |

```
Thr Thr Gln Tyr Phe Leu Gly Ile Lys Ile Ser Glu Asp Ile Leu Glu
            645                 650                 655 agt gat gaa ata tat ggt tta tgc aac tgt acc ggt aga gtc ctt cga   2016
Ser Asp Glu Ile Tyr Gly Leu Cys Asn Cys Thr Gly Arg Val Leu Arg
            660                 665                 670 atc ctt aat gat tta caa gat tcc aag aaa gaa caa aag gag gac tca   2064
Ile Leu Asn Asp Leu Gln Asp Ser Lys Lys Glu Gln Lys Glu Asp Ser
            675                 680                 685 gta act ata gtc aca tta cta atg aaa agt atg tct gag gaa gaa gct   2112
Val Thr Ile Val Thr Leu Leu Met Lys Ser Met Ser Glu Glu Glu Ala
        690                 695                 700 ata atg aag ata aag gaa atc ttg gaa atg aat aga aga gag tta ttg   2160
Ile Met Lys Ile Lys Glu Ile Leu Glu Met Asn Arg Arg Glu Leu Leu
705                 710                 715                 720 aaa atg gtt tta gtt caa aaa aag gga agc caa ttg cct caa ata tgc   2208
Lys Met Val Leu Val Gln Lys Lys Gly Ser Gln Leu Pro Gln Ile Cys
                725                 730                 735 aaa gat ata ttt tgg agg aca agc aac tgg gct gat ttc att tat tta   2256
Lys Asp Ile Phe Trp Arg Thr Ser Asn Trp Ala Asp Phe Ile Tyr Leu
            740                 745                 750 caa act gat gga tat aga att gca gag gaa atg aag aat cac att gat   2304
Gln Thr Asp Gly Tyr Arg Ile Ala Glu Glu Met Lys Asn His Ile Asp
            755                 760                 765 gaa gtc ttt tac aaa cca ctc aat cat taa                           2334
Glu Val Phe Tyr Lys Pro Leu Asn His
        770                 775

<210> SEQ ID NO 4
<211> LENGTH: 777
<212> TYPE: PRT
<213> ORGANISM: Solanum habrochaites

<400> SEQUENCE: 4

Met Ile Val Gly Tyr Arg Ser Thr Ile Ile Thr Leu Ser His Pro Lys
1               5                   10                  15

Leu Gly Asn Gly Lys Thr Ile Ser Ser Asn Ala Ile Phe Gln Arg Ser
            20                  25                  30

Cys Arg Val Arg Cys Ser His Ser Thr Pro Ser Ser Met Asn Gly Phe
        35                  40                  45

Glu Asp Ala Arg Asp Arg Ile Arg Glu Ser Phe Gly Lys Val Glu Leu
    50                  55                  60

Ser Pro Ser Ser Tyr Asp Thr Ala Trp Val Ala Met Val Pro Ser Lys
65                  70                  75                  80

His Ser Leu Asn Glu Pro Cys Phe Pro Gln Cys Leu Asp Trp Ile Ile
                85                  90                  95

Glu Asn Gln Arg Glu Asp Gly Ser Trp Gly Leu Asn Pro Ser His Pro
            100                 105                 110

Leu Leu Leu Lys Asp Ser Leu Ser Ser Thr Leu Ala Cys Leu Leu Ala
        115                 120                 125

Leu Thr Lys Trp Arg Val Gly Asp Glu Gln Ile Lys Arg Gly Leu Gly
    130                 135                 140

Phe Ile Glu Thr Gln Ser Trp Ala Ile Asp Asn Lys Asp Gln Ile Ser
145                 150                 155                 160

Pro Leu Gly Phe Glu Ile Ile Phe Pro Ser Met Ile Lys Ser Ala Glu
                165                 170                 175

Lys Leu Asn Leu Asn Leu Ala Ile Asn Lys Arg Asp Ser Thr Ile Lys
            180                 185                 190

Arg Ala Leu Gln Asn Glu Phe Thr Arg Asn Ile Glu Tyr Met Ser Glu
```

-continued

```
            195                 200                 205
Gly Val Gly Glu Leu Cys Asp Trp Lys Glu Ile Ile Lys Leu His Gln
    210                 215                 220

Arg Gln Asn Gly Ser Leu Phe Asp Ser Pro Ala Thr Thr Ala Ala Ala
225                 230                 235                 240

Leu Ile Tyr His Gln His Asp Lys Lys Cys Tyr Glu Tyr Leu Asn Ser
        245                 250                 255

Ile Leu Gln Gln His Lys Asn Trp Val Pro Thr Met Tyr Pro Thr Lys
            260                 265                 270

Ile His Ser Leu Leu Cys Leu Val Asp Thr Leu Gln Asn Leu Gly Val
        275                 280                 285

His Arg His Phe Lys Ser Glu Ile Lys Lys Ala Leu Asp Glu Ile Tyr
    290                 295                 300

Arg Leu Trp Gln Gln Lys Asn Glu Gln Ile Phe Ser Asn Val Thr His
305                 310                 315                 320

Cys Ala Met Ala Phe Arg Leu Leu Arg Met Ser Tyr Tyr Asp Val Ser
                325                 330                 335

Ser Asp Glu Leu Ala Glu Phe Val Asp Glu His Phe Phe Ala Ile
            340                 345                 350

Ser Gly Lys Tyr Thr Ser His Val Glu Ile Leu Glu Leu His Lys Ala
        355                 360                 365

Ser Gln Leu Ala Ile Asp His Glu Lys Asp Asp Ile Leu Asp Lys Ile
    370                 375                 380

Asn Asn Trp Thr Arg Thr Phe Met Glu Gln Lys Leu Leu Asn Asn Gly
385                 390                 395                 400

Phe Ile Asp Arg Met Ser Lys Lys Glu Val Glu Leu Ala Leu Arg Lys
                405                 410                 415

Phe Tyr Thr Ile Ser Asp Leu Ala Glu Asn Arg Arg Cys Ile Lys Ser
            420                 425                 430

Tyr Glu Glu Asn Phe Lys Ile Leu Lys Ala Ala Tyr Arg Ser Pro
        435                 440                 445

Asn Ile Tyr Asn Lys Asp Leu Phe Ile Phe Ser Ile Arg Asn Phe Glu
450                 455                 460

Leu Cys Gln Ala Gln His Gln Glu Glu Leu Gln Gln Phe Lys Arg Trp
465                 470                 475                 480

Phe Glu Asp Tyr Arg Leu Asp Gln Leu Gly Ile Ala Glu Arg Tyr Ile
                485                 490                 495

His Asp Thr Tyr Leu Cys Ala Val Ile Val Pro Glu Pro Glu Leu
            500                 505                 510

Ser Asp Ala Arg Leu Leu Tyr Ala Lys Tyr Val Leu Leu Thr Ile
        515                 520                 525

Val Asp Asp Gln Phe Asp Ser Phe Ala Ser Thr Asp Glu Cys Leu Asn
    530                 535                 540

Ile Ile Glu Leu Val Glu Arg Trp Asp Asp Tyr Ala Ser Val Gly Tyr
545                 550                 555                 560

Lys Ser Glu Lys Val Lys Val Phe Phe Ser Thr Leu Tyr Lys Ser Ile
                565                 570                 575

Glu Glu Leu Val Thr Ile Ala Glu Ile Lys Gln Gly Arg Ser Val Lys
            580                 585                 590

Asn His Leu Leu Asn Leu Trp Leu Glu Leu Val Lys Leu Met Leu Met
        595                 600                 605

Glu Arg Val Glu Trp Phe Ser Gly Lys Thr Ile Pro Ser Ile Glu Glu
    610                 615                 620
```

-continued

| Tyr | Leu | Tyr | Val | Thr | Ser | Ile | Thr | Phe | Gly | Ala | Arg | Leu | Ile | Pro | Leu |
| 625 | | | | | 630 | | | | | 635 | | | | | 640 |

Thr Thr Gln Tyr Phe Leu Gly Ile Lys Ile Ser Glu Asp Ile Leu Glu
                    645                    650                    655

Ser Asp Glu Ile Tyr Gly Leu Cys Asn Cys Thr Gly Arg Val Leu Arg
        660                    665                    670

Ile Leu Asn Asp Leu Gln Asp Ser Lys Lys Glu Gln Lys Glu Asp Ser
            675                    680                    685

Val Thr Ile Val Thr Leu Leu Met Lys Ser Met Ser Glu Glu Glu Ala
      690                    695                    700

Ile Met Lys Ile Lys Glu Ile Leu Glu Met Asn Arg Arg Glu Leu Leu
705                    710                    715                    720

Lys Met Val Leu Val Gln Lys Lys Gly Ser Gln Leu Pro Gln Ile Cys
                725                    730                    735

Lys Asp Ile Phe Trp Arg Thr Ser Asn Trp Ala Asp Phe Ile Tyr Leu
            740                    745                  750

Gln Thr Asp Gly Tyr Arg Ile Ala Glu Glu Met Lys Asn His Ile Asp
            755                    760                    765

Glu Val Phe Tyr Lys Pro Leu Asn His
770                    775

<210> SEQ ID NO 5
<211> LENGTH: 31
<212> TYPE: DNA
<213> ORGANISM: artificial sequence
<220> FEATURE:
<223> OTHER INFORMATION: primer

<400> SEQUENCE: 5
accatgggtt ctttggttct tcaatgttgg a                                    31

<210> SEQ ID NO 6
<211> LENGTH: 34
<212> TYPE: DNA
<213> ORGANISM: artificial sequence
<220> FEATURE:
<223> OTHER INFORMATION: primer

<400> SEQUENCE: 6
actcgagata tgtgtgtcca ccaaaacgtc tatg                                 34

<210> SEQ ID NO 7
<211> LENGTH: 31
<212> TYPE: DNA
<213> ORGANISM: artificial sequence
<220> FEATURE:
<223> OTHER INFORMATION: primer

<400> SEQUENCE: 7
tccatggtag ttggctatag aagcacaatc a                                    31

<210> SEQ ID NO 8
<211> LENGTH: 34
<212> TYPE: DNA
<213> ORGANISM: artificial sequence
<220> FEATURE:
<223> OTHER INFORMATION: primer

<400> SEQUENCE: 8
tctcgagcat aaattcaaat tgagggatta atga                                 34

<210> SEQ ID NO 9

```
<211> LENGTH: 31
<212> TYPE: DNA
<213> ORGANISM: artificial sequence
<220> FEATURE:
<223> OTHER INFORMATION: primer

<400> SEQUENCE: 9
accatgggtt ctttggttct tcaatgttgg a                                31

<210> SEQ ID NO 10
<211> LENGTH: 34
<212> TYPE: DNA
<213> ORGANISM: artificial sequence
<220> FEATURE:
<223> OTHER INFORMATION: primer

<400> SEQUENCE: 10
actcgagata tgtgtgtcca ccaaaacgtc tatg                             34
```